United States Patent
Mao et al.

(10) Patent No.: US 11,447,808 B2
(45) Date of Patent: Sep. 20, 2022

(54) BIOSYNTHETIC PRODUCTION OF STEVIOL GLYCOSIDE REBAUDIOSIDE I VIA VARIANT ENZYMES

(71) Applicant: Conagen Inc., Bedford, MA (US)

(72) Inventors: Guohong Mao, Burlington, MA (US); Michael Batten, Westford, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 236 days.

(21) Appl. No.: 16/506,892

(22) Filed: Jul. 9, 2019

(65) Prior Publication Data

US 2020/0002742 A1 Jan. 2, 2020

Related U.S. Application Data

(63) Continuation-in-part of application No. PCT/US2019/021876, filed on Mar. 12, 2019.

(60) Provisional application No. 62/695,252, filed on Jul. 9, 2018, provisional application No. 62/682,260, filed on Jun. 8, 2018, provisional application No. 62/641,590, filed on Mar. 12, 2018.

(51) Int. Cl.
| | |
|---|---|
| *C12P 19/56* | (2006.01) |
| *C12N 9/10* | (2006.01) |
| *C12N 15/82* | (2006.01) |

(52) U.S. Cl.
CPC ............ *C12P 19/56* (2013.01); *C12N 9/1081* (2013.01); *C12N 15/8245* (2013.01); *C12Y 204/01013* (2013.01); *C12Y 204/99* (2013.01)

(58) Field of Classification Search
CPC . A23L 2/60; A23L 27/36; A23L 27/33; A23L 27/30; A23L 29/30; A61K 31/704; C12N 15/81; C12N 2523/00; C12N 9/1051; C12N 9/1048; C12N 9/1062; C12N 9/10; C12N 9/1081; C12N 15/52; C12N 15/8245; C12N 9/0071; C12N 9/1085; C12N 9/90; C12N 1/16; C12N 9/0042; C12N 9/0073; C12N 15/63; C12N 15/746; C12N 15/8243; C12N 15/8257; C12N 1/185; C12N 9/0032; C12N 9/88; C12P 19/56; C12P 19/18; C12P 15/00; C12P 19/44; C12P 33/00; C12P 7/40; A23V 2002/00; A23V 2250/258; A23V 2250/262; C07H 15/256; C07H 15/24; C07H 1/00; C07H 1/06; C07H 1/08; C07H 3/06; C12Y 204/01013; C12Y 204/01; C12Y 204/01017; C12Y 204/99; C12Y 106/02004; C12Y 114/13078; C12Y 114/13079; C12Y 114/14; C12Y 205/01029; C12Y 302/01021; C12Y 402/03019; C12Y 505/01013; C07K 2319/00; C07K 14/245; Y02P 20/582; A24B 15/10; A24B 15/302; A23K 20/163; C12R 2001/865; G01N 2030/027; G01N 30/02

See application file for complete search history.

(56) References Cited

U.S. PATENT DOCUMENTS

| | | | | |
|---|---|---|---|---|
| 8,791,253 | B2* | 7/2014 | Prakash | C07H 1/08 |
| | | | | 536/128 |
| 9,631,215 | B2* | 4/2017 | Houghton-Larsen | C12P 19/44 |
| 9,783,566 | B2* | 10/2017 | Mao | C07H 15/24 |
| 9,908,913 | B2* | 3/2018 | Mao | A23L 33/10 |
| 9,957,540 | B2 | 5/2018 | Mikkelsen et al. | |
| 10,435,730 | B2* | 10/2019 | Houghton-Larsen | C12N 9/88 |
| 10,463,062 | B2* | 11/2019 | Philippe | A23L 2/60 |
| 10,570,163 | B2* | 2/2020 | Mao | A23L 2/60 |
| 10,724,062 | B2* | 7/2020 | Mao | C12P 19/44 |
| 10,883,130 | B2 | 1/2021 | Mao et al. | |
| 2006/0143729 | A1 | 6/2006 | Alexandrov et al. | |
| 2012/0107362 | A1 | 5/2012 | Hofmann et al. | |
| 2014/0329281 | A1* | 11/2014 | Houghton-Larsen | C12P 19/44 |
| | | | | 435/78 |
| 2014/0357588 | A1* | 12/2014 | Markosyan | A24B 15/302 |
| | | | | 514/34 |
| 2017/0112176 | A1 | 4/2017 | Markosyan et al. | |
| 2017/0275666 | A1 | 9/2017 | Prakash et al. | |
| 2017/0303865 | A1* | 10/2017 | Kojima | G06T 7/0012 |
| 2017/0321238 | A1* | 11/2017 | Houghton-Larsen | |
| | | | | C12N 9/0073 |
| 2017/0332673 | A1 | 11/2017 | Philippe et al. | |
| 2017/0362267 | A1* | 12/2017 | Mao | C12N 9/1062 |
| 2018/0163244 | A1* | 6/2018 | Anderson | C12P 19/56 |
| 2019/0338332 | A1 | 11/2019 | Tao et al. | |
| 2020/0087695 | A1 | 3/2020 | Mao et al. | |
| 2021/0189448 | A1 | 6/2021 | Mao et al. | |

FOREIGN PATENT DOCUMENTS

| | | |
|---|---|---|
| WO | WO 2015/171555 A1 | 11/2015 |
| WO | WO 2016/028899 A1 | 2/2016 |
| WO | PCT/US2019/021876 | 7/2019 |
| WO | PCT/US2020/041394 | 10/2020 |

OTHER PUBLICATIONS

U.S. Appl. No. 17/109,473, filed Dec. 2, 2020, Mao et al.
International Search Report and Written Opinion dated Jul. 17, 2019 for Application No. PCT/US2019/021876.
Branden et al., Introduction to Protein Structure. 1991. Garland Publishing Inc., Eds. p. 247.
Chaturvedula et al., Isolation, NMR Spectral Analysis and Hydrolysis Studies of a Hepta Pyranosyl Diterpene Glycoside from Stevia rebaudiana Bertoni. Biomolecules. Sep. 30, 2013;3(4):733-40. doi: 10.3390/biom3040733.

(Continued)

*Primary Examiner* — Michelle F. Paguio Frising

(74) *Attorney, Agent, or Firm* — Wolf, Greenfield & Sacks, P.C.; W. John Keyes

(57) ABSTRACT

The present invention relates, at least in part, to the production of steviol glycoside rebaudioside I through the use of variant UGT enzymes having activity to transfer a glucosyl group from UDP-glucose to rebaudioside A to produce rebaudioside I.

17 Claims, 5 Drawing Sheets

Specification includes a Sequence Listing.

(56) References Cited

OTHER PUBLICATIONS

Sadowski et al., The Sequence-Structure Relationship and Protein Function Prediction. Curr Opin Struct Biol. Jun. 2009;19(3):357-62. doi: 10.1016/j.sbi.2009.03.008. Epub May 4, 2009.
Seffernick et al., Melamine Deaminase and Atrazine Chlorohydrolase: 98 Percent Identical but Functionally Different. J Bacteriol. Apr. 2001;183(8):2405-10. doi: 10.1128/JB.183.8.2405-2410.2001.
Tang et al., Identification of Dehalobacter Reductive Dehalogenases That Catalyse Dechlorination of Chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Witkowski et al., Conversion of a Beta-Ketoacyl Synthase to a Malonyl Decarboxylase by Replacement of the Active-Site Cysteine With Glutamine. Biochemistry. Sep. 7, 1999;38(36):11643-50. doi: 10.1021/bi990993h.

* cited by examiner

SEQUENCE LISTING

<160> NUMBER OF SEQ ID NOS: 12

<210> SEQ ID NO 1
<211> LENGTH: 458
<212> TYPE: PRT
<213> ORGANISM: Artificial Sequence
<220> FEATURE:
<223> OTHER INFORMATION: Synthetic polypeptide

<400> SEQUENCE: 1

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Ala Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 2
<211> LENGTH: 1377
<212> TYPE: DNA
<213> ORGANISM: Artificial Sequence
<220> FEATURE:
<223> OTHER INFORMATION: Synthetic polynucleotide

<400> SEQUENCE: 2
atggagaata agacagaaac aaccgtaaga cggaggcgga ggattatctt gttccctgta     60
ccatttcagg gccatattaa tccgatcctc aattagcaa acgtcctcta ctccaaggga    120
ttttcaataa caatcttcca tactaacttt aacaagccta aaacgagtaa ttatcctcac    180
tttacattca ggttcattct agacaacgac cctcaggatg agcgtatctc aaatttacct    240
acgcatggcc ccttggcagg tatgcgaata ccaataatca atgagcatgg agccgatgaa    300

```
ctccgtcgcg agttagagct tctcatgctc gcaagtgagg aagacgagga agtttcgtgc    360
ctaataactg atgcgctttg gtacttcgcc caatcagtcg cagactcact gaatctacgc    420
cgtttggtcc ttatgacaag ttcattattc aactttcacg cacatgtatc actgccgcaa    480
tttgacgagt tgggttacct ggacccggat gacaaaacgc gattggagga caagcgtcg     540
ggcttcccca tgctgaaagt caagatatt aagagcgctt atagtaattg caaattgcg      600
aaagaaattc tcggaaaaat gataaagcaa accaaagcgt cctctggagt aatctggaac    660
tccttcaagg agttagagga atctgaactt gaaacggtca tcagagaaat ccccgctccc    720
tcgttcttaa ttccactacc caagcacctt actgcaagta gcagttccct cctagatcat    780
gaccgaaccg tgtttcagtg gctggatcag caaccccgt cgtcagttct atatgtaagc     840
tttggagta cttcggaagt ggatgaaaag gacttcttag agattgcgcg agggctcgtg     900
gatagcaaac agagcttcct gtgggtagtg agaccgggat tcgttaaggg ctcgacgtgg    960
gtcgagccgt tgccagatgg ttttctaggg gagagaggga gaatcgtgaa atgggttcca   1020
cagcaagagg ttttggctca cggagctata ggggcctttt ggacccactc tggttggaat   1080
tctactcttg aaagtgtctg tgaaggcgtt ccaatgatat tttctgattt tgggcttgac   1140
cagcctctaa acgctcgcta tgtctcgat gtgttgaagg ttggcgtgta cctggagaat    1200
ggttgggaaa ggggggaaat tgccaacgcc atacgccggg taatggtgga cgaggaaggt   1260
gagtacatac gtcagaacgc tcgggttta aaacaaaaag cggacgtcag ccttatgaag    1320
ggaggtagct cctatgaatc cctagaatcc ttggtaagct atatatcttc gttataa      1377
```

<210> SEQ ID NO 3
<211> LENGTH: 458
<212> TYPE: PRT
<213> ORGANISM: Artificial Sequence
<220> FEATURE:
<223> OTHER INFORMATION: Synthetic polypeptide

<400> SEQUENCE: 3

```
Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Leu Leu
    50                  55                  60

Asp His Asp Arg Thr Val Phe Gln Trp Leu Asp Gln Gln Pro Ser
65                  70                  75                  80

Ser Val Leu Tyr Val Ser Phe Gly Ser Thr Ser Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175
```

```
Pro Met Ile Phe Ser Asp Phe Gly Leu Asp Gln Pro Leu Asn Ala Arg
            180                 185                 190
Tyr Met Ser Asp Val Leu Lys Val Gly Val Tyr Leu Glu Asn Gly Trp
        195                 200                 205
Glu Arg Gly Glu Ile Ala Asn Ala Ile Arg Arg Val Met Val Asp Glu
    210                 215                 220
Glu Gly Glu Tyr Ile Arg Gln Asn Ala Arg Val Leu Lys Gln Lys Ala
225                 230                 235                 240
Asp Val Ser Leu Met Lys Gly Ser Ser Tyr Glu Ser Leu Glu Ser
                245                 250                 255
Leu Val Ser Tyr Ile Ser Ser Leu Glu Asn Lys Thr Glu Thr Thr Val
                260                 265                 270
Arg Arg Arg Arg Ile Ile Leu Phe Pro Val Pro Phe Gln Gly His
    275                 280                 285
Ile Asn Pro Ile Leu Gln Leu Ala Asn Val Leu Tyr Ser Lys Gly Phe
        290                 295                 300
Ser Ile Thr Ile Phe His Thr Asn Phe Asn Lys Pro Lys Thr Ser Asn
305                 310                 315                 320
Tyr Pro His Phe Thr Phe Arg Phe Ile Leu Asp Asn Asp Pro Gln Asp
                325                 330                 335
Glu Arg Ile Ser Asn Leu Pro Thr His Gly Pro Leu Ala Gly Met Arg
            340                 345                 350
Ile Pro Ile Ile Asn Glu His Gly Ala Asp Glu Leu Arg Arg Glu Leu
        355                 360                 365
Glu Leu Leu Met Leu Ala Ser Glu Glu Asp Glu Val Ser Cys Leu
    370                 375                 380
Ile Thr Asp Ala Leu Trp Tyr Phe Ala Gln Ser Val Ala Asp Ser Leu
385                 390                 395                 400
Asn Leu Arg Arg Leu Val Leu Met Thr Ser Ser Leu Phe Asn Phe His
                405                 410                 415
Ala His Val Ser Leu Pro Gln Phe Asp Glu Leu Gly Tyr Leu Asp Pro
            420                 425                 430
Asp Asp Lys Thr Arg Leu Glu Glu Gln Ala Ser Gly Phe Pro Met Leu
        435                 440                 445
Lys Val Lys Asp Ile Lys Ser Ala Tyr Ser
        450                 455

<210> SEQ ID NO 4
<211> LENGTH: 1377
<212> TYPE: DNA
<213> ORGANISM: Artificial Sequence
<220> FEATURE:
<223> OTHER INFORMATION: Synthetic polynucleotide

<400> SEQUENCE: 4
atgaactggc aaatcctgaa agaaatcctg ggtaaaatga tcaaacaaac caaagcgtcg    60
tcgggcgtta tctggaactc cttcaaagaa ctgaagaat cagaactgga aaccgttatt   120
cgcgaaatcc cggctccgtc gttcctgatt ccgctgccga acatctgac gcgagcagc    180 agcagcctgc tggatcacga ccgtacggtc tttcagtggc tggatcagca accgccgtca   240
tcggtgctgt atgtttcatt cggtagcacc tctgaagtcg atgaaaaaga ctttctggaa   300
atcgctcgcg gcctggtgga tagtaaacag tccttcctgt gggtggttcg tccgggtttt   360
gtgaaaggca gcacgtgggt tgaaccgctg ccggatggct tcctgggtga acgcggccgt   420
attgtcaaat gggtgccgca gcaagaagtg ctggcacatg gtgctatcgg cgcgtttttgg   480
```

```
acccactctg gttggaacag tacgctggaa tccgtttgcg aaggtgtccc gatgattttc    540
agcgattttg gcctggacca gccgctgaat gcccgctata tgtctgatgt tctgaaagtc    600
ggtgtgtacc tggaaaacgg ttgggaacgt ggcgaaattg cgaatgccat ccgtcgcgtt    660
atggtcgatg aagaaggcga atacattcgc cagaacgctc gtgtcctgaa acaaaaagcg    720
gacgtgagcc tgatgaaagg cggtagctct tatgaatcac tggaatcgct ggttagctac    780
atcagttccc tggaaaataa aaccgaaacc acggtgcgtc gccgtcgccg tattatcctg    840
ttcccggttc cgtttcaggg tcatattaac ccgatcctgc aactggcgaa tgttctgtat    900
tcaaaaggct tttcgatcac catcttccat acgaacttca acaaaccgaa aaccagtaac    960
tacccgcact ttacgttccg ctttattctg ataacgacc cgcaggatga acgtatctcc   1020
aatctgccga cccacggccc gctggccggt atgcgcattc cgattatcaa tgaacacggt   1080
gcagatgaac tgcgccgtga actggaactg ctgatgctgg ccagtgaaga agatgaagaa   1140
gtgtcctgtc tgatcaccga cgcactgtgg tatttcgccc agagcgttgc agattctctg   1200
aacctgcgcc gtctggtcct gatgacgtca tcgctgttca attttcatgc gcacgtttct   1260
ctgccgcaat tgatgaact gggctacctg gacccggatg acaaaacccg tctggaagaa   1320
caagccagtg gttttccgat gctgaaagtc aaagacatta atccgccta ttcgtaa      1377
```

<210> SEQ ID NO 5
<211> LENGTH: 475
<212> TYPE: PRT
<213> ORGANISM: Artificial Sequence
<220> FEATURE:
<223> OTHER INFORMATION: Synthetic polypeptide

<400> SEQUENCE: 5

```
Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Leu Leu
    50                  55                  60

Asp His Asp Arg Thr Val Phe Gln Trp Leu Asp Gln Gln Pro Pro Ser
65                  70                  75                  80

Ser Val Leu Tyr Val Ser Phe Gly Ser Thr Ser Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175

Pro Met Ile Phe Ser Asp Phe Gly Leu Asp Gln Pro Leu Asn Ala Arg
            180                 185                 190

Tyr Met Ser Asp Val Leu Lys Val Gly Val Tyr Leu Glu Asn Gly Trp
        195                 200                 205
```

```
Glu Arg Gly Glu Ile Ala Asn Ala Ile Arg Arg Val Met Val Asp Glu
            210                 215                 220

Glu Gly Glu Tyr Ile Arg Gln Asn Ala Arg Val Leu Lys Gln Lys Ala
225                 230                 235                 240

Asp Val Ser Leu Met Lys Gly Ser Ser Tyr Glu Ser Leu Glu Ser
                245                 250                 255

Leu Val Ser Tyr Ile Ser Ser Leu Tyr Lys Asp Asp Ser Gly Tyr Ser
                260                 265                 270

Ser Ser Tyr Ala Ala Ala Ala Gly Met Glu Asn Lys Thr Glu Thr Thr
            275                 280                 285

Val Arg Arg Arg Arg Ile Ile Leu Phe Pro Val Pro Phe Gln Gly
290                 295                 300

His Ile Asn Pro Ile Leu Gln Leu Ala Asn Val Leu Tyr Ser Lys Gly
305                 310                 315                 320

Phe Ser Ile Thr Ile Phe His Thr Asn Phe Asn Lys Pro Lys Thr Ser
                325                 330                 335

Asn Tyr Pro His Phe Thr Phe Arg Phe Ile Leu Asp Asn Asp Pro Gln
            340                 345                 350

Asp Glu Arg Ile Ser Asn Leu Pro Thr His Gly Pro Leu Ala Gly Met
            355                 360                 365

Arg Ile Pro Ile Ile Asn Glu His Gly Ala Asp Glu Leu Arg Arg Glu
370                 375                 380

Leu Glu Leu Leu Met Leu Ala Ser Glu Glu Asp Glu Glu Val Ser Cys
385                 390                 395                 400

Leu Ile Thr Asp Ala Leu Trp Tyr Phe Ala Gln Ser Val Ala Asp Ser
                405                 410                 415

Leu Asn Leu Arg Arg Leu Val Leu Met Thr Ser Ser Leu Phe Asn Phe
            420                 425                 430

His Ala His Val Ser Leu Pro Gln Phe Asp Glu Leu Gly Tyr Leu Asp
            435                 440                 445

Pro Asp Asp Lys Thr Arg Leu Glu Glu Gln Ala Ser Gly Phe Pro Met
    450                 455                 460

Leu Lys Val Lys Asp Ile Lys Ser Ala Tyr Ser
465                 470                 475

<210> SEQ ID NO 6
<211> LENGTH: 1428
<212> TYPE: DNA
<213> ORGANISM: Artificial Sequence
<220> FEATURE:
<223> OTHER INFORMATION: Synthetic polynucleotide

<400> SEQUENCE: 6
atgaactggc aaatcctgaa agaaatcctg ggtaaaatga tcaaacaaac caaagcgtcg      60
tcgggcgtta tctggaactc cttcaaagaa ctggaagaat cagaactgga accgttatt     120 cgcgaaatcc cggctccgtc gttcctgatt ccgctgccga acatctgac cgcgagcagc     180 agcagcctgc tggatcacga ccgtacggtc tttcagtggc tggatcagca accgccgtca    240
tcggtgctgt atgtttcatt cggtagcacc tctgaagtcg atgaaaaaga ctttctggaa    300
atcgctcgcg gcctggtgga tagtaaacag tccttcctgt gggtggttcg tccgggtttt    360
gtgaaaggca gcacgtgggt tgaaccgctg ccggatggct tcctgggtga acgcggccgt    420
attgtcaaat gggtgccgca gcaagaagtg ctggcacatg gtgctatcgg cgcgttttgg    480
acccactctg gttggaacag tacgctggaa tccgtttgcg aaggtgtccc gatgatttc    540
```

```
agcgattttg gcctggacca gccgctgaat gcccgctata tgtctgatgt tctgaaagtc    600
ggtgtgtacc tggaaaacgg ttgggaacgt ggcgaaattg cgaatgccat ccgtcgcgtt    660
atggtcgatg aagaaggcga atacattcgc cagaacgctc gtgtcctgaa acaaaaagcg    720
gacgtgagcc tgatgaaagg cggtagctct tatgaatcac tggaatcgct ggttagctac    780
atcagttccc tgtacaaaga tgacagcggt tatagcagca gctatgcggc ggcggcgggt    840
atggaaaata aaaccgaaac cacggtgcgt cgccgtcgcc gtattatcct gttcccggtt    900
ccgtttcagg gtcatattaa cccgatcctg caactggcga atgttctgta ttcaaaaggc    960
ttttcgatca ccatcttcca tacgaacttc aacaaaccga aaccagtaa ctacccgcac   1020 tttacgttcc gctttattct ggataacgac ccgcaggatg aacgtatctc caatctgccg   1080
acccacggcc cgctggccgg tatgcgcatt ccgattatca atgaacacgg tgcagatgaa   1140
ctgcgccgtg aactggaact gctgatgctg gccagtgaag aagatgaaga agtgtcctgt   1200
ctgatcaccg acgcactgtg gtatttcgcc cagagcgttg cagattctct gaacctgcgc   1260
cgtctggtcc tgatgacgtc atcgctgttc aattttcatg cgcacgtttc tctgccgcaa   1320
tttgatgaac tgggctacct ggacccggat gacaaaaccc gtctggaaga acaagccagt   1380
ggttttccga tgctgaaagt caaagacatt aaatccgcct attcgtaa              1428
```

<210> SEQ ID NO 7
<211> LENGTH: 1268
<212> TYPE: PRT
<213> ORGANISM: Artificial Sequence
<220> FEATURE:
<223> OTHER INFORMATION: Synthetic polypeptide

<400> SEQUENCE: 7

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

```
Lys Gln Thr Lys Ala Ser Ser Gly Val Ile Trp Asn Ser Phe Lys Glu
210                 215                 220
Leu Glu Glu Ser Glu Leu Glu Thr Val Ile Arg Glu Ile Pro Ala Pro
225                 230                 235                 240
Ser Phe Leu Ile Pro Leu Pro Lys His Leu Thr Ala Ser Ser Ser Ser
            245                 250                 255
Leu Leu Asp His Asp Arg Thr Val Phe Gln Trp Leu Asp Gln Gln Pro
            260                 265                 270
Pro Ser Ser Val Leu Tyr Val Ser Phe Gly Ser Thr Ser Glu Val Asp
        275                 280                 285
Glu Lys Asp Phe Leu Glu Ile Ala Arg Gly Leu Val Asp Ser Lys Gln
290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
            325                 330                 335
Lys Trp Val Pro Gln Gln Glu Val Leu Ala His Gly Ala Ile Gly Ala
            340                 345                 350
Phe Trp Thr His Ser Gly Trp Asn Ser Thr Leu Glu Ser Val Cys Glu
            355                 360                 365
Gly Val Pro Met Ile Phe Ser Asp Phe Gly Leu Asp Gln Pro Leu Asn
370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
            405                 410                 415
Asp Glu Glu Gly Glu Tyr Ile Arg Gln Asn Ala Arg Val Leu Lys Gln
            420                 425                 430
Lys Ala Asp Val Ser Leu Met Lys Gly Gly Ser Ser Tyr Glu Ser Leu
            435                 440                 445
Glu Ser Leu Val Ser Tyr Ile Ser Ser Leu Gly Ser Gly Ala Asn Ala
450                 455                 460
Glu Arg Met Ile Thr Arg Val His Ser Gln Arg Glu Arg Leu Asn Glu
465                 470                 475                 480
Thr Leu Val Ser Glu Arg Asn Glu Val Leu Ala Leu Leu Ser Arg Val
            485                 490                 495
Glu Ala Lys Gly Lys Gly Ile Leu Gln Gln Asn Gln Ile Ile Ala Glu
            500                 505                 510
Phe Glu Ala Leu Pro Glu Gln Thr Arg Lys Lys Leu Glu Gly Gly Pro
            515                 520                 525
Phe Phe Asp Leu Leu Lys Ser Thr Gln Glu Ala Ile Val Leu Pro Pro
        530                 535                 540
Trp Val Ala Leu Ala Val Arg Pro Arg Pro Gly Val Trp Glu Tyr Leu
545                 550                 555                 560
Arg Val Asn Leu His Ala Leu Val Val Glu Glu Leu Gln Pro Ala Glu
            565                 570                 575
Phe Leu His Phe Lys Glu Glu Leu Val Asp Gly Val Lys Asn Gly Asn
            580                 585                 590
Phe Thr Leu Glu Leu Asp Phe Glu Pro Phe Asn Ala Ser Ile Pro Arg
            595                 600                 605
Pro Thr Leu His Lys Tyr Ile Gly Asn Gly Val Asp Phe Leu Asn Arg
610                 615                 620
```

-continued

His Leu Ser Ala Lys Leu Phe His Asp Lys Glu Ser Leu Leu Pro Leu
625                 630                 635                 640

Leu Lys Phe Leu Arg Leu His Ser His Gln Gly Lys Asn Leu Met Leu
            645                 650                 655

Ser Glu Lys Ile Gln Asn Leu Asn Thr Leu Gln His Thr Leu Arg Lys
                660                 665                 670

Ala Glu Glu Tyr Leu Ala Glu Leu Lys Ser Glu Thr Leu Tyr Glu Glu
            675                 680                 685

Phe Glu Ala Lys Phe Glu Glu Ile Gly Leu Glu Arg Gly Trp Gly Asp
        690                 695                 700

Asn Ala Glu Arg Val Leu Asp Met Ile Arg Leu Leu Leu Asp Leu Leu
705                 710                 715                 720

Glu Ala Pro Asp Pro Cys Thr Leu Glu Thr Phe Leu Gly Arg Val Pro
                725                 730                 735

Met Val Phe Asn Val Val Ile Leu Ser Pro His Gly Tyr Phe Ala Gln
                740                 745                 750

Asp Asn Val Leu Gly Tyr Pro Asp Thr Gly Gly Gln Val Val Tyr Ile
            755                 760                 765

Leu Asp Gln Val Arg Ala Leu Glu Ile Glu Met Leu Gln Arg Ile Lys
770                 775                 780

Gln Gln Gly Leu Asn Ile Lys Pro Arg Ile Leu Ile Leu Thr Arg Leu
785                 790                 795                 800

Leu Pro Asp Ala Val Gly Thr Thr Cys Gly Glu Arg Leu Glu Arg Val
            805                 810                 815

Tyr Asp Ser Glu Tyr Cys Asp Ile Leu Arg Val Pro Phe Arg Thr Glu
            820                 825                 830

Lys Gly Ile Val Arg Lys Trp Ile Ser Arg Phe Glu Val Trp Pro Tyr
        835                 840                 845

Leu Glu Thr Tyr Thr Glu Asp Ala Ala Val Glu Leu Ser Lys Glu Leu
        850                 855                 860

Asn Gly Lys Pro Asp Leu Ile Ile Gly Asn Tyr Ser Asp Gly Asn Leu
865                 870                 875                 880

Val Ala Ser Leu Leu Ala His Lys Leu Gly Val Thr Gln Cys Thr Ile
            885                 890                 895

Ala His Ala Leu Glu Lys Thr Lys Tyr Pro Asp Ser Asp Ile Tyr Trp
        900                 905                 910

Lys Lys Leu Asp Asp Lys Tyr His Phe Ser Cys Gln Phe Thr Ala Asp
        915                 920                 925

Ile Phe Ala Met Asn His Thr Asp Phe Ile Ile Thr Ser Thr Phe Gln
930                 935                 940

Glu Ile Ala Gly Ser Lys Glu Thr Val Gly Gln Tyr Glu Ser His Thr
945                 950                 955                 960

Ala Phe Thr Leu Pro Gly Leu Tyr Arg Val Val His Gly Ile Asp Val
            965                 970                 975

Phe Asp Pro Lys Phe Asn Ile Val Ser Pro Gly Ala Asp Met Ser Ile
        980                 985                 990

Tyr Phe Pro Tyr Thr Glu Glu Lys Arg Arg Leu Thr Lys Phe His Ser
        995                 1000                1005

Glu Ile Glu Glu Leu Leu Tyr Ser Asp Val Glu Asn Lys Glu His
    1010                1015                1020

Leu Cys Val Leu Lys Asp Lys Lys Lys Pro Ile Leu Phe Thr Met
    1025                1030                1035

```
Ala Arg Leu Asp Arg Val Lys Asn Leu Ser Gly Leu Val Glu Trp
1040                1045                1050

Tyr Gly Lys Asn Thr Arg Leu Arg Glu Leu Ala Asn Leu Val Val
    1055                1060                1065

Val Gly Gly Asp Arg Arg Lys Glu Ser Lys Asp Asn Glu Glu Lys
        1070                1075                1080

Ala Glu Met Lys Lys Met Tyr Asp Leu Ile Glu Tyr Lys Leu
    1085                1090                1095

Asn Gly Gln Phe Arg Trp Ile Ser Ser Gln Met Asp Arg Val Arg
    1100                1105                1110

Asn Gly Glu Leu Tyr Arg Tyr Ile Cys Asp Thr Lys Gly Ala Phe
    1115                1120                1125

Val Gln Pro Ala Leu Tyr Glu Ala Phe Gly Leu Thr Val Val Glu
    1130                1135                1140

Ala Met Thr Cys Gly Leu Pro Thr Phe Ala Thr Cys Lys Gly Gly
    1145                1150                1155

Pro Ala Glu Ile Ile Val His Gly Lys Ser Gly Phe His Ile Asp
    1160                1165                1170

Pro Tyr His Gly Asp Gln Ala Ala Asp Thr Leu Ala Asp Phe Phe
    1175                1180                1185

Thr Lys Cys Lys Glu Asp Pro Ser His Trp Asp Glu Ile Ser Lys
    1190                1195                1200

Gly Gly Leu Gln Arg Ile Glu Glu Lys Tyr Thr Trp Gln Ile Tyr
    1205                1210                1215

Ser Gln Arg Leu Leu Thr Leu Thr Gly Val Tyr Gly Phe Trp Lys
    1220                1225                1230

His Val Ser Asn Leu Asp Arg Leu Glu Ala Arg Arg Tyr Leu Glu
    1235                1240                1245

Met Phe Tyr Ala Leu Lys Tyr Arg Pro Leu Ala Gln Ala Val Pro
    1250                1255                1260

Leu Ala Gln Asp Asp
    1265

<210> SEQ ID NO 8
<211> LENGTH: 3807
<212> TYPE: DNA
<213> ORGANISM: Artificial Sequence
<220> FEATURE:
<223> OTHER INFORMATION: Synthetic polynucleotide

<400> SEQUENCE: 8
atggagaata agacagaaac aaccgtaaga cggaggcgga ggattatctt gttccctgta    60
ccatttcagg gccatattaa tccgatcctc caattagcaa acgtcctcta ctccaaggga   120
ttttcaataa caatcttcca tactaacttt aacaagccta aacgagtaa ttatcctcac    180 tttacattca ggttcattct agacaacgac cctcaggatg agcgtatctc aaatttacct   240
acgcatggcc ccttggcagg tatgcgaata ccaataatca atgagcatgg agccgatgaa   300
ctccgtcgcg agttagagct tctcatgctc gcaagtgagg aagacgagga gtttcgtgc   360 ctaataactg atgcgctttg gtacttcgcc caatcagtcg cagactcact gaatctacgc   420
cgtttggtcc ttatgacaag ttcattattc aactttcacg cacatgtatc actgccgcaa   480
tttgacgagt tgggttacct ggacccggat gacaaaacgc gattggagga caagcgtcg   540 ggcttccccca tgctgaaagt caagatatt aagagcgctt atagtaattg gcaaattctg   600
aaagaaattc tcggaaaaat gataaagcaa accaaagcgt cctctggagt aatctggaac   660
```

```
tccttcaagg agttagagga atctgaactt gaaacggtca tcagagaaat ccccgctccc      720
tcgttcttaa ttccactacc caagcacctt actgcaagta gcagttccct cctagatcat      780
gaccgaaccg tgtttcagtg gctggatcag caaccccgt cgtcagttct atatgtaagc       840
tttgggagta cttcggaagt ggatgaaaag gacttcttag agattgcgcg agggctcgtg      900
gatagcaaac agagcttcct gtgggtagtg agaccgggat tcgttaaggg ctcgacgtgg      960
gtcgagccgt tgccagatgg ttttctaggg gagagaggga gaatcgtgaa atgggttcca     1020
cagcaagagg ttttggctca cggagctata ggggcctttt ggacccactc tggttggaat     1080
tctactcttg aaagtgtctg tgaaggcgtt ccaatgatat tttctgattt tgggcttgac     1140
cagcctctaa acgctcgcta tatgtctgat gtgttgaagg ttggcgtgta cctggagaat     1200
ggttgggaaa gggggaaat tgccaacgcc atacgccggg taatggtgga cgaggaaggt      1260
gagtacatac gtcagaacgc tcgggtttta aaacaaaaag cggacgtcag ccttatgaag     1320
ggaggtagct cctatgaatc cctagaatcc ttggtaagct atatatcttc gttaggttct     1380
ggtgcaaacg ctgaacgtat gataacgcgc gtccacagcc aacgtgagcg tttgaacgaa     1440
acgcttgttt ctgagagaaa cgaagtcctt gccttgcttt ccagggttga agccaaaggt     1500
aaaggtattt tacaacaaaa ccagatcatt gctgaattcg aagctttgcc tgaacaaacc     1560
cggaagaaac ttgaaggtgg tccttctttt gaccttctca aatccactca ggaagcaatt     1620
gtgttgccac catgggttgc tctagctgtg aggccaaggc ctggtgtttg gaatactta     1680 cgagtcaatc tccatgctct tgtcgttgaa gaactccaac ctgctgagtt tcttcatttc     1740
aaggaagaac tcgttgatgg agttaagaat ggtaatttca ctcttgagct tgatttcgag     1800
ccattcaatg cgtctatccc tcgtccaaca ctccacaaat acattggaaa tggtgttgac     1860
ttccttaacc gtcatttatc ggctaagctc ttccatgaca aggagagttt gcttccattg     1920
cttaagttcc ttcgtcttca cagccaccag ggcaagaacc tgatgttgag cgagaagatt     1980
cagaacctca acactctgca acacaccttg aggaaagcag aagagtatct agcagagctt     2040
aagtccgaaa cactgtatga agagtttgag gccaagtttg aggagattgg tcttgagagg     2100
ggatggggag acaatgcaga gcgtgtcctt gacatgatac gtcttctttt ggaccttctt     2160
gaggcgcctg atccttgcac tcttgagact tttcttggaa gagtaccaat ggtgttcaac     2220
gttgtgatcc tctctccaca tggttacttt gctcaggaca atgttcttgg ttaccctgac     2280
actggtggac aggttgttta cattcttgat caagttcgtg ctctggagat agagatgctt     2340
caacgtatta gcaacaagg actcaacatt aaaccaagga ttctcattct aactcgactt      2400
ctacctgatg cggtaggaac tacatgcggt gaacgtctcg agagagttta tgattctgag     2460
tactgtgata ttcttcgtgt gcccttcaga acagagaagg gtattgttcg caaatggatc     2520
tcaaggttcg aagtctggcc atatctagag acttacaccg aggatgctgc ggttgagcta     2580
tcgaaagaat tgaatggcaa gcctgacctt atcattggta actacagtga tggaaatctt     2640
gttgcttctt tattggctca caaacttggt gtcactcagt gtaccattgc tcatgctctt     2700
gagaaaacaa agtacccgga ttctgatatc tactggaaga gcttgacga caagtaccat     2760 ttctcatgcc agtcactgc ggatattttc gcaatgaacc acactgattt catcatcact      2820
agtactttcc aagaaattgc tggaagcaaa gaaactgttg ggcagtatga agccacaca      2880 gcctttactc ttcccggatt gtatcgagtt gttcacggga ttgatgtgtt tgatcccaag     2940
ttcaacattg tctctcctgg tgctgatatg agcatctact tcccttacac agaggagaag     3000
cgtagattga ctaagttcca ctctgagatc gaggagctcc tctacagcga tgttgagaac     3060
```

```
aaagagcact tatgtgtgct caaggacaag aagaagccga ttctcttcac aatggctagg    3120
cttgatcgtg tcaagaactt gtcaggtctt gttgagtggt acgggaagaa cacccgcttg    3180
cgtgagctag ctaacttggt tgttgttgga ggagacagga ggaaagagtc aaaggacaat    3240
gaagagaaag cagagatgaa gaaaatgtat gatctcattg aggaatacaa gctaaacggt    3300
cagttcaggt ggatctcctc tcagatggac cgggtaagga acggtgagct gtaccggtac    3360
atctgtgaca ccaagggtgc ttttgtccaa cctgcattat atgaagcctt tgggttaact    3420
gttgtggagg ctatgacttg tggtttaccg actttcgcca cttgcaaagg tggtccagct    3480
gagatcattg tgcacggtaa atcgggtttc cacattgacc cttaccatgg tgatcaggct    3540
gctgatactc ttgctgattt cttcaccaag tgtaaggagg atccatctca ctgggatgag    3600
atctcaaaag gagggcttca gaggattgag gagaaataca cttggcaaat ctattcacag    3660
aggctcttga cattgactgg tgtgtatgga ttctggaagc atgtctcgaa ccttgaccgt    3720
cttgaggctc gccgttacct tgaaatgttc tatgcattga agtatcgccc attggctcag    3780
gctgttcctc ttgcacaaga tgattga                                        3807
```

<210> SEQ ID NO 9
<211> LENGTH: 458
<212> TYPE: PRT
<213> ORGANISM: Stevia rebaudiana

<400> SEQUENCE: 9

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240
```

| | | | | | | | | | | | |
|---|---|---|---|---|---|---|---|---|---|---|---|
|Ser|Phe|Leu|Ile|Pro|Leu|Pro|Lys|His|Leu|Thr|Ala|Ser|Ser|Ser|Ser|
| | | |245| | | |250| | | |255|
|Leu|Leu|Asp|His|Asp|Arg|Thr|Val|Phe|Gln|Trp|Leu|Asp|Gln|Gln|Pro|
| | | |260| | | |265| | | |270|
|Pro|Ser|Ser|Val|Leu|Tyr|Val|Ser|Phe|Gly|Ser|Thr|Ser|Glu|Val|Asp|
| | | |275| | | |280| | | |285|
|Glu|Lys|Asp|Phe|Leu|Glu|Ile|Ala|Arg|Gly|Leu|Val|Asp|Ser|Lys|Gln|
| | | |290| | | |295| | | |300|
|Ser|Phe|Leu|Trp|Val|Val|Arg|Pro|Gly|Phe|Val|Lys|Gly|Ser|Thr|Trp|
|305| | | |310| | | |315| | | |320|
|Val|Glu|Pro|Leu|Pro|Asp|Gly|Phe|Leu|Gly|Glu|Arg|Gly|Arg|Ile|Val|
| | | |325| | | |330| | | |335|
|Lys|Trp|Val|Pro|Gln|Gln|Glu|Val|Leu|Ala|His|Gly|Ala|Ile|Gly|Ala|
| | | |340| | | |345| | | |350|
|Phe|Trp|Thr|His|Ser|Gly|Trp|Asn|Ser|Thr|Leu|Glu|Ser|Val|Cys|Glu|
| | | |355| | | |360| | | |365|
|Gly|Val|Pro|Met|Ile|Phe|Ser|Asp|Phe|Gly|Leu|Asp|Gln|Pro|Leu|Asn|
| | | |370| | | |375| | | |380|
|Ala|Arg|Tyr|Met|Ser|Asp|Val|Leu|Lys|Val|Gly|Val|Tyr|Leu|Glu|Asn|
|385| | | |390| | | |395| | | |400|
|Gly|Trp|Glu|Arg|Gly|Glu|Ile|Ala|Asn|Ala|Ile|Arg|Arg|Val|Met|Val|
| | | |405| | | |410| | | |415|
|Asp|Glu|Glu|Gly|Glu|Tyr|Ile|Arg|Gln|Asn|Ala|Arg|Val|Leu|Lys|Gln|
| | | |420| | | |425| | | |430|
|Lys|Ala|Asp|Val|Ser|Leu|Met|Lys|Gly|Gly|Ser|Ser|Tyr|Glu|Ser|Leu|
| | | |435| | | |440| | | |445|
|Glu|Ser|Leu|Val|Ser|Tyr|Ile|Ser|Ser|Leu|
| | | |450| | | |455|

<210> SEQ ID NO 10
<211> LENGTH: 1377
<212> TYPE: DNA
<213> ORGANISM: Stevia rebaudiana

<400> SEQUENCE: 10

```
atggagaata agacagaaac aaccgtaaga cggaggcgga ggattatctt gttccctgta      60
ccatttcagg gccatattaa tccgatcctc caattagcaa acgtcctcta ctccaaggga     120
ttttcaataa caatcttcca tactaacttt aacaagccta aaacgagtaa ttatcctcac     180
tttacattca ggttcattct agacaacgac cctcaggatg agcgtatctc aaatttacct     240
acgcatggcc ccttggcagg tatgcgaata ccaataatca atgagcatgg agccgatgaa     300
ctccgtcgcg agttagagct tctcatgctc gcaagtgagg aagacgagga agtttcgtgc     360
ctaataactg atgcgctttg gtacttcgcc caatcagtcg cagactcact gaatctacgc     420
cgtttggtcc ttatgacaag ttcattattc aactttcacg cacatgtatc actgccgcaa     480
tttgacgagt tgggttacct ggacccggat gacaaaacgc gattggagga caagcgtcg      540
ggcttcccca tgctgaaagt caaagatatt aagagcgctt atagtaattg gcaaattctg     600
aaagaaattc tcggaaaaat gataaagcaa accaaagcgt cctctggagt aatctggaac     660
tccttcaagg agttagagga atctgaactt gaaacggtca tcagagaaat ccccgctccc     720
tcgttcttaa ttccactacc caagcacctt actgcaagta gcagttccct cctagatcat     780
gaccgaaccg tgtttcagtg gctggatcag caaccccgt cgtcagttct atatgtaagc     840
tttgggagta cttcggaagt ggatgaaaag gacttcttag agattgcgcg agggctcgtg     900
```

-continued

```
gatagcaaac agagcttcct gtgggtagtg agaccgggat tcgttaaggg ctcgacgtgg      960
gtcgagccgt tgccagatgg ttttctaggg gagagaggga gaatcgtgaa atgggttcca     1020
cagcaagagg ttttggctca cggagctata ggggcctttt ggacccactc tggttggaat     1080
tctactcttg aaagtgtctg tgaaggcgtt ccaatgatat tttctgattt tgggcttgac     1140
cagcctctaa acgctcgcta tatgtctgat gtgttgaagg ttggcgtgta cctggagaat     1200
ggttgggaaa ggggggaaat tgccaacgcc atacgccggg taatggtgga cgaggaaggt     1260
gagtacatac gtcagaacgc tcgggtttta aaacaaaaag cggacgtcag ccttatgaag     1320
ggaggtagct cctatgaatc cctagaatcc ttggtaagct atatatcttc gttataa        1377
```

<210> SEQ ID NO 11
<211> LENGTH: 808
<212> TYPE: PRT
<213> ORGANISM: Arabidopsis thaliana

<400> SEQUENCE: 11

```
Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
                85                  90                  95

Trp Glu Tyr Leu Arg Val Asn Leu His Ala Leu Val Val Glu Glu Leu
            100                 105                 110

Gln Pro Ala Glu Phe Leu His Phe Lys Glu Glu Leu Val Asp Gly Val
        115                 120                 125

Lys Asn Gly Asn Phe Thr Leu Glu Leu Asp Phe Glu Pro Phe Asn Ala
    130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
    210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Cys Thr Leu Glu Thr Phe Leu
            260                 265                 270

Gly Arg Val Pro Met Val Phe Asn Val Val Ile Leu Ser Pro His Gly
        275                 280                 285
```

-continued

```
Tyr Phe Ala Gln Asp Asn Val Leu Gly Tyr Pro Asp Thr Gly Gly Gln
    290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
            340                 345                 350

Leu Glu Arg Val Tyr Asp Ser Glu Tyr Cys Asp Ile Leu Arg Val Pro
        355                 360                 365

Phe Arg Thr Glu Lys Gly Ile Val Arg Lys Trp Ile Ser Arg Phe Glu
    370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
    450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Ser Ile Tyr Phe Pro Tyr Thr Glu Glu Lys Arg Arg Leu Thr
    530                 535                 540

Lys Phe His Ser Glu Ile Glu Glu Leu Leu Tyr Ser Asp Val Glu Asn
545                 550                 555                 560

Lys Glu His Leu Cys Val Leu Lys Asp Lys Lys Pro Ile Leu Phe
                565                 570                 575

Thr Met Ala Arg Leu Asp Arg Val Lys Asn Leu Ser Gly Leu Val Glu
            580                 585                 590

Trp Tyr Gly Lys Asn Thr Arg Leu Arg Glu Leu Ala Asn Leu Val Val
        595                 600                 605

Val Gly Gly Asp Arg Arg Lys Glu Ser Lys Asp Asn Glu Glu Lys Ala
    610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
            660                 665                 670

Leu Tyr Glu Ala Phe Gly Leu Thr Val Val Glu Ala Met Thr Cys Gly
        675                 680                 685

Leu Pro Thr Phe Ala Thr Cys Lys Gly Gly Pro Ala Glu Ile Ile Val
    690                 695                 700
```

```
His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
        755                 760                 765

Tyr Gly Phe Trp Lys His Val Ser Asn Leu Asp Arg Leu Glu Ala Arg
    770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805

<210> SEQ ID NO 12
<211> LENGTH: 2427
<212> TYPE: DNA
<213> ORGANISM: Arabidopsis thaliana

<400> SEQUENCE: 12
atggcaaacg ctgaacgtat gattacccgt gtccactccc aacgcgaacg cctgaacgaa      60
accctggtgt cggaacgcaa cgaagttctg gcactgctga gccgtgtgga agctaagggc     120
aaaggtattc tgcagcaaaa ccagattatc gcggaatttg aagccctgcc ggaacaaacc     180
cgcaaaaagc tggaaggcgg tccgtttttc gatctgctga atctacgca ggaagcgatc     240 gttctgccgc cgtgggtcgc actggcagtg cgtccgcgtc cgggcgtttg gaatatctg     300 cgtgtcaacc tgcatgcact ggtggttgaa gaactgcagc cggctgaatt ctgcacttc     360 aaggaagaac tggttgacgg cgtcaaaaac ggtaatttta ccctggaact ggattttgaa     420
ccgttcaatg ccagtatccc gcgtccgacg ctgcataaat atattggcaa cggtgtggac     480
tttctgaatc gccatctgag cgcaaagctg ttccacgata agaatctct gctgccgctg     540 ctgaaattcc tgcgtctgca tagtcaccag ggcaagaacc tgatgctgtc cgaaaaaatt     600
cagaacctga tacccctgca cacacgctg cgcaaggcgg aagaatacct ggccgaactg     660
aaaagtgaaa ccctgtacga agaattcgaa gcaaagttcg aagaaattgg cctggaacgt     720
ggctggggtg acaatgctga acgtgttctg gatatgatcc gtctgctgct ggacctgctg     780
gaagcaccgg acccgtgcac cctggaaacg tttctgggtc gcgtgccgat ggttttcaac     840
gtcgtgattc tgtccccgca tggctatttt gcacaggaca atgtgctggg ttacccggat     900 accgcggtc aggttgtcta tattctggat caagttcgtg cgctggaaat tgaaatgctg     960
cagcgcatca agcagcaagg cctgaacatc aaaccgcgta ttctgatcct gacccgtctg    1020
ctgccggatg cagttggtac cacgtgcggt gaacgtctgg aacgcgtcta tgacagcgaa    1080
tactgtgata ttctgcgtgt cccgtttcgc accgaaaagg gtattgtgcg taatggatc     1140 agtcgcttcg aagtttggcc gtatctggaa acctacacgg aagatgcggc cgtggaactg    1200
tccaaggaac tgaatggcaa accggacctg attatcggca actatagcga tggtaatctg    1260
gtcgcatctc tgctggctca taactgggt gtgacccagt gcacgattgc acacgctctg    1320
gaaaagacca atatcccgga ttcagacatc tactggaaaa agctggatga caaatatcat    1380
ttttcgtgtc agttcaccgc ggacattttt gccatgaacc acacggattt tattatcacc    1440
agtacgttcc aggaaatcgc gggctccaaa gaaaccgtgg gtcaatacga atcacatacc    1500
```

-continued

```
gccttcacgc tgccgggcct gtatcgtgtg gttcacggta tcgatgtttt tgacccgaaa    1560
ttcaatattg tcagtccggg cgcggatatg tccatctatt ttccgtacac cgaagaaaag    1620
cgtcgcctga cgaaattcca ttcagaaatt gaagaactgc tgtactcgga cgtggaaaac    1680
aaggaacacc tgtgtgttct gaaagataaa aagaaaccga tcctgtttac catggcccgt    1740
ctggatcgcg tgaagaatct gtcaggcctg gttgaatggt atggtaaaaa cacgcgtctg    1800
cgcgaactgg caaatctggt cgtggttggc ggtgaccgtc gcaaggaatc gaaagataac    1860
gaagaaaagg ctgaaatgaa gaaaatgtac gatctgatcg aagaatacaa gctgaacggc    1920
cagtttcgtt ggatcagctc tcaaatggac cgtgtgcgca atggcgaact gtatcgctac    1980
atttgcgata ccaagggtgc gtttgttcag ccggcactgt acgaagcttt cggcctgacc    2040
gtcgtggaag ccatgacgtg cggtctgccg acctttgcga cgtgtaaagg cggtccggcc    2100
gaaattatcg tgcatggcaa atctggtttc catatcgatc cgtatcacgg tgatcaggca    2160
gctgacaccc tggcggattt ctttacgaag tgtaaagaag acccgtcaca ctgggatgaa    2220
atttcgaagg gcggtctgca acgtatcgaa gaaaaatata cctggcagat ttacagccaa    2280
cgcctgctga ccctgacggg cgtctacggt ttttggaaac atgtgtctaa tctggatcgc    2340
ctggaagccc gtcgctatct ggaaatgttt tacgcactga agtatcgccc gctggcacaa    2400
gccgttccgc tggcacagga cgactaa                                        2427
```

BIOSYNTHETIC PRODUCTION OF STEVIOL GLYCOSIDE REBAUDIOSIDE I VIA VARIANT ENZYMES

RELATED APPLICATIONS

This application is a continuation-in-part of International patent application PCT/US2019/021876, filed Mar. 12, 2019 and entitled "BIOSYNTHETIC PRODUCTION OF STEVIOL GLYCOSIDES REBAUDIOSIDE J AND REBAUDIOSIDE N," which claims the benefit under 35 U.S.C. § 119(e) of U.S. Provisional Patent Application No. 62/641,590, filed Mar. 12, 2018 and entitled "BIOSYNTHETIC PRODUCTION OF STEVIOL GLYCOSIDES REBAUDIOSIDE J AND REBAUDIOSIDE N", and U.S. Provisional Patent Application No. 62/682,260, filed Jun. 8, 2018 and entitled "BIOSYNTHETIC PRODUCTION OF STEVIOL GLYCOSIDES REBAUDIOSIDE J AND REBAUDIOSIDE N", the entire contents of which are incorporated herein by reference. This application also claims the benefit under 35 U.S.C. § 119(e) of U.S. provisional application Ser. No. 62/695,252, filed Jul. 9, 2018, and entitled "BIOSYNTHETIC PRODUCTION OF STEVIOL GLYCOSIDE REBAUDIOSIDE I VIA VARIANT ENZYMES," the entire contents of which are incorporated herein by reference.

FIELD OF THE INVENTION

The field of the invention relates, at least in part, to methods and processes useful in the production of a specific steviol glycoside via a biosynthetic pathway engineered into selected microorganisms. More specifically, the present disclosure provides for the production of Rebaudioside I ("Reb I") using previously unknown enzymes and/or enzyme variants.

SUMMARY OF THE INVENTION

The present invention is focused, at least in part, on the production of Reb I from Reb A and/or the production of Reb I through the use of modified enzymes.

The specific and directed glycosylation of rebaudioside A (at the C-19-O-glucose) can produce rebaudioside Reb I. The synthetic steps to produce Reb I from Reb A enzymatically have been accomplished herein with alternative enzymes. As described in more detail below, it has been found that mutations in the domains in UGT76G1 can cause specific alterations of glucosylation activity.

In addition, methods of producing rebaudioside I from stevioside through rebaudioside A at high titer and/or with a reduction in cost are provided.

The present invention encompasses a method of producing Reb I from Reb A. In particular, the current invention provides for the production of steviol glycoside rebaudioside I "Reb I" which is identified as (13-[(2-O-β-D-glucopyranosyl-3-O-β-D-glucopyranosyl-β-D-glucopyranosyl)oxy] ent-kaur-16-en-19-oic acid-[(3-O-β-D-glucopyranosyl-β-D-glucopyranosyl) ester].

Provided herein, inter alia, are methods for synthesizing rebaudioside I, the method comprising preparing a reaction mixture comprising: (a) a steviol glycoside composition comprising rebaudioside A; (b) a substrate selected from the group consisting of sucrose, uridine diphosphate (UDP), uridine diphosphate-glucose (UDP-glucose), and combinations thereof; and (c) a UDP-glycosyltransferase enzyme comprising the amino acid sequence of SEQ ID NO: 1; and incubating the reaction mixture for a sufficient time to produce rebaudioside I.

In some embodiments of any one of the methods provided, the UDP-glycosyltransferase enzyme used in the methods described herein comprises an amino acid sequence that is at least 80% (e.g., at least 80%, at least 85%, at least 90%, at least 95%, at least 96%, at least 97%, at least 98%, at least 99% or 100%) identical to SEQ ID NO: 1.

In one aspect, any one of the enzymes described herein is provided.

In some embodiments of any one of the methods provided, the steviol glycoside composition is *Stevia* extract.

In some embodiments of any one of the methods provided, the methods described herein further comprises adding a sucrose synthase to the reaction mixture. In some embodiments of any one of the methods provided, the sucrose synthase is an *Arabidopsis thaliana* sucrose synthase 1 (AtSUS1) comprising the amino acid sequence of SEQ ID NO: 11.

In some embodiments of any one of the methods provided, the sucrose synthase used in the methods described herein comprises an amino acid sequence that is at least 80% (e.g., at least 80%, at least 85%, at least 90%, at least 95%, at least 96%, at least 97%, at least 98%, at least 99% or 100%) identical to SEQ ID NO: 11.

In some embodiments of any one of the methods provided, the reaction mixture is in vitro, i.e., the method described herein is performed in vitro. For in vitro reactions, the UDP-glycosyltransferase enzyme and/or the sucrose synthase can be added to the in vitro reaction mixture.

In some embodiments of any one of the methods provided, the reaction mixture is a cell-based reaction mixture, i.e., the reaction is performed in a cell. For cell-based reactions, the UDP-glycosyltransferase enzyme and/or the sucrose synthase can be expressed in a host cell.

In some embodiments of any one of the methods provided, the UDP-glycosyltransferase enzyme and/or the sucrose synthase are expressed from nucleotide sequences encoding UDP-glycosyltransferase enzyme and/or the sucrose synthase, respectively. As such, in some embodiments of any one of the methods provided, the host cell comprises a nucleotide sequence having at least 80% (e.g., at least 80%, at least 85%, at least 90%, at least 95%, at least 96%, at least 97%, at least 98%, at least 99% or 100%) identity to SEQ ID NO: 2. In some embodiments of any one of the methods provided, the host cell further comprises a nucleotide sequence having at least 80% (e.g., at least 80%, at least 85%, at least 90%, at least 95%, at least 96%, at least 97%, at least 98%, at least 99% or 100%) identity to SEQ ID NO: 12.

In one aspect, a nucleic acid comprising any one of the sequences described herein is provided.

In some embodiments of any one of the methods provided, the host cell is selected from the group consisting of a yeast, a non-steviol glycoside producing plant, an alga, a fungus, and a bacterium.

In some embodiments of any one of the methods provided, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea*; and *Clostridium*.

In some embodiments of any one of the methods provided, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum vulgare*; switchgrass (*Panicum vigratum*); *Brachypodium* spp.; *Brassica* spp.; and *Crambe abyssinica*.

In some embodiments of any one of the methods provided, the host cell is a bacterial cell (e.g., an *E. coli* cell).

In some embodiments of any one of the methods provided, the host cell is a yeast cell (e.g., a *Saccharomyces cerevisiae* cell).

In one aspect, any one of the host cells described herein is provided.

In some embodiments of any one of the methods provided, the substrate is UDP-glucose. In some embodiments of any one of the methods provided, the UDP-glycose is generated in situ (e.g., from UDP and sucrose using a sucrose synthase).

In some embodiments of any one of the methods provided, the rebaudioside A has a concentration of 15 to 50 g/L (e.g., 15-50, 20-50, 30-50, 40-50, 15-40, 20-40, 30-40, 30-50, 30-40, or 40-50 g/L) in the reaction mixture.

In some embodiments of any one of the methods provided, the reaction mixture has a pH range of 6.5 to 9.5 (e.g., 6.5, 7, 7.5, 8, 8.5, 9, or 9.5) at a temperature of 35° C. to 45° C. (e.g., 35° C., 36° C., 37° C., 38° C., 39° C., 40° C., 41° C., 42° C., 43° C., 44° C., or 45° C.).

In some embodiments of any one of the methods provided, the method further comprises isolating crude rebaudioside I (e.g., using a microporous adsorption resin).

In one aspect, a composition comprising any one of the rebaudioside I compositions described herein is provided.

In some embodiments of any one of the methods provided, the method described herein further comprises crystallizing the crude rebaudioside I to obtain rebaudioside I with a purity of greater than 98% (e.g., 98%, 99%, or 99.9%).

Aspects of the present disclosure provide a mutant of the UGT76G1 enzyme comprising a L200A mutation (herein termed the "LA mutant"). The L200A mutation is relative to SEQ ID NO: 9. In some embodiments of any one of the compositions or methods provided, the LA mutant comprises an amino acid sequence having at least 80% (e.g., at least 80%, at least 85%, at least 90%, at least 95%, at least 96%, at least 97%, at least 98%, at least 99% or 100%) identity to SEQ ID NO: 1, and comprises the L200A mutation. In some embodiments of any one of the compositions or methods provided, the LA mutant comprises the amino acid sequence of SEQ ID NO: 1. In one aspect, a composition comprising any one of the mutants described herein is provided.

In terms of product/commercial utility there are several dozen products containing steviol glycosides on the market in the United States and can be used in everything from analgesics to pest repellents as well as in foods and as a dietary supplement. Products containing steviol glycosides can be aerosols, liquids, gels or granular formulations and such products are provided in some embodiments.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of embodiments of this invention.

DETAILED DESCRIPTION OF CERTAIN EMBODIMENTS

Figure 1:
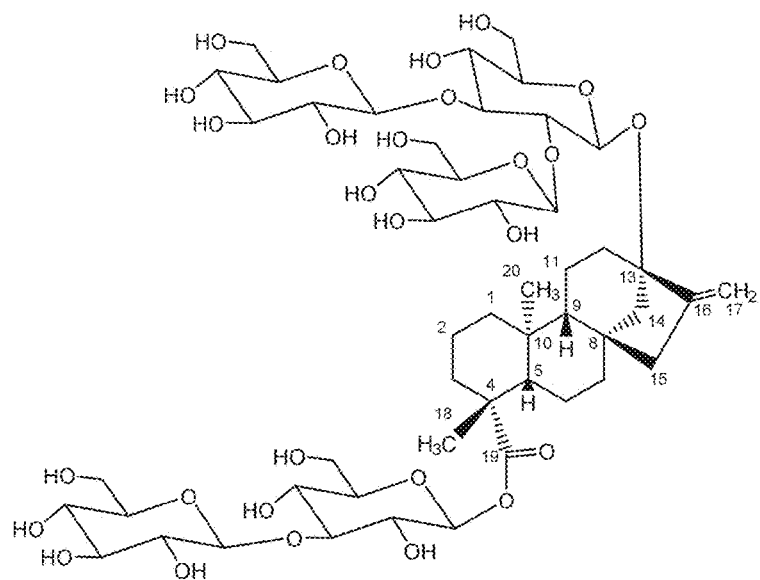
FIG. 1 shows the chemical structure of rebaudioside I ("Reb I"), ($C_{50}H_{80}O_{28}$), 13-[(2-O-β-D-glucopyranosyl-3-O-β-D-glucopyranosyl)-β-D-glucopyranosyl)oxy]-ent-kaur-16-en-19oic acid-(3-O-β-D-glucopyranosyl)-β-D-glucopyranosyl), ester.

Steviol Glycosides are a class of chemical compounds responsible for the sweet taste of the leaves of the South American plant *Stevia rebaudiana* (Asteraceae), and can be used as sweeteners in food, feed and beverages.

Definitions

Cellular system includes any cell that provides for the expression of ectopic proteins. It includes bacteria, yeast, plant cells and animal cells or any cellular system that would allow the genetic transformation with the selected genes and thereafter the biosynthetic production of the desired steviol glycosides from steviol. It includes both prokaryotic and eukaryotic cells. It also includes the in vitro expression of proteins based on cellular components, such as ribosomes. *E. coli* is a preferred microbial system in an embodiment of any one of the methods provided herein.

Coding sequence is to be given its ordinary and customary meaning to a person of ordinary skill in the art and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current invention yeast as claimed herein are eukaryotic, single-celled microorganisms classified as members of the fungus kingdom. Yeasts are unicellular organisms which evolved from multicellular ancestors but with some species useful for the current invention being those that have the ability to develop multicellular characteristics by forming strings of connected budding cells known as pseudohyphae or false hyphae.

The names of the UGT enzymes used in the present disclosure are consistent with the nomenclature system adopted by the UGT Nomenclature Committee (Mackenzie et al., "*The UDP glycosyltransferase gene super family: recommended nomenclature updated based on evolutionary divergence*," PHARMACOGENETICS, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number 1.

Structural Terms:

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art and is used without limitation to describe the relationship between nucleotide bases that are capable of hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences.

The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxy inosine residues. A nucleic acid sequence and all of its degenerate variants will express the same amino acid or polypeptide.

The terms "polypeptide," "protein, ' and "peptide" are to be given their respective ordinary' and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term 'polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it can affect the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the craft, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "transformed".

The terms "transformed," "transgenic," and "recombinant," when used herein in connection with host cells, are to be given their respective ordinary and customary meanings to a person of ordinary skill in the art and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The present invention relates to the production of a steviol glycoside of interest, Reb I from using UGT enzymes to allow that conversion. The subject technology provides recombinant polypeptides with UDP glycosyltransferase activities, such as 1,3-19-O-glucose glycosylation activity and 1,3-13-O-glucose glycosylation activity for synthesizing steviol glycosides. The recombinant polypeptide of the subject technology is useful for the biosynthesis of steviol glycoside compounds. In the present disclosure, UDP-glycosyltransferase (UGT) refers to an enzyme that transfers a sugar residue from an activated donor molecule (typically UDP-glucose) to an acceptor molecule. The 1,3-19-O-glucose glycosylation activity refers to an enzymatic activity that transfers a sugar moiety to the C-3' of the 19-O glucose moiety of rebaudioside A to produce rebaudioside I (Reb I) (FIG. 1).

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by Greene Publishing and Wiley-Interscience, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family 1 GT enzymes, also known as the UDP glycosyltransferases (UGTs), transfer UDP-activated sugar moieties to specific acceptor molecules. These are the molecules that transfer such sugar moieties in the steviol glycosides to create various rebaudiosides. Each of these UGTs have their own activity profile and preferred structure locations where they transfer their activated sugar moieties.

Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

Several molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities, thereby generating blunt ended DNA segments. The blunt-ended segments are then incubated with a large molar excess of linker molecules in the presence of an enzyme that can catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference to the extent it is consistent herewith).

In an embodiment, to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a *Petunia* plant cell.

Microbial host cell expression systems and expression vectors containing regulatory sequences that direct highlevel expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll alb binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Precursor Synthesis to Reb I

As previously stated steviol glycosides are the chemical compounds responsible for the sweet taste of the leaves of the South American plant *Stevia rebaudiana* (Asteraceae) and in the plant *Rubus chingii* (Rosaceae). These compounds are glycosylated diterpenes. Specifically, their molecules can be viewed as a steviol molecule, with its hydroxyl hydrogen atom replaced by a glucose molecule to form an ester, and a hydroxyl hydrogen with combinations of glucose and rhamnose to form an acetal.

One method of making the compounds of interest in the current invention is to take common or inexpensive precursors such as steviol or rubososide derived chemically or produced via biosynthesis in engineered microbes such as bacteria and/or yeast and to synthesize targeted steviol glycosides through known or inexpensive methods, such as Reb I.

Aspects of the present invention relate to methods involving recombinantly expressing enzymes in a microbial system capable of producing steviol. In general, such enzymes may include: a copalyl diphosphate synthase (CPS), a kaurene synthase (KS) and a geranylgeranyl diphosphate to synthase (GGPPS) enzyme. This should occur in a microbial strain that expresses an endogenous isoprenoid synthesis pathway, such as the non-mevalonate (MEP) pathway or the mevalonic acid pathway (MVA). In some embodiments, the cell is a bacterial cell, including *E. coli*, or yeast cell such as a *Saccharomyces* cell, *Pichia* cell, or a *Yarrowia* cell. In some embodiments, the cell is an algal cell or a plant cell.

Thereafter, the precursor is recovered from the fermentation culture for use in chemical synthesis. Typically, this is steviol though it can be kaurene, or a steviol glycoside from the cell culture. In some embodiments, the steviol, kaurene and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments, the steviol glycoside is selected from rebaudioside A, rebaudioside B, rebaudioside C, rebaudioside D, rebaudioside E, rebaudioside I or dulcoside A. In some embodiments, the terpenoid produced is steviobioside or stevioside. It should also be appreciated that in some embodiments, at least one enzymatic step, such as one or more glycosylation steps, are performed ex vivo.

Part of the invention is the production of the steviol glycoside that is then subject to further enzymatic conversion to Reb I. According to the current invention, the biosynthesis for the conversion of microbially produced steviol to a desired steviol glycosides (here Reb I) occurs when the diterpenoid steviol is converted from rubososide and stevioside using multi-step chemical assembly of sugar moiety into the steviol backbone. In some embodiments, the biosynthesis for the conversion of Reb A to Reb I occurs by reacting Reb A with a glucose donor moiety in the presence of a recombinant polypeptide having glucosyltransferase activity. In some embodiments, the glucose donor moiety is generated in situ. In some embodiments, the glucose donor moiety is added to the reaction. For example, in some embodiments, an enzyme identified as UGT76G1 (SEQ ID NO: 10) can convert Reb A to Reb I. In some embodiments, a UGT76G1 mutant comprising a mutation L200A relative to SEQ ID NO: 9 (referred to herein as the "LA mutant," the mutant having an amino acid sequence of SEQ ID NO: 1) can convert Reb A to Reb I. It was demonstrated herein that the LA mutant has increased activity in converting Reb A to Reb I.

Biosynthesis of Steviol Glycosides

As described herein, the recombinant polypeptides of the present technology have UDP-glycosyltransferase activities and are useful for developing biosynthetic methods for preparing steviol glycosides that are either not present in nature or typically of low abundance in natural sources, such as rebaudioside I and rebaudioside M, respectively. The recombinant polypeptides of the present technology have UDP-glycosyltransferase activities, are useful for developing biosynthetic methods for preparing novel steviol glycosides, such as rebaudioside I and reaching the synthetic production of rebaudioside M.

The substrate can be any natural or synthetic compound capable of being converted into a steviol glycoside compound in a reaction catalyzed by one or more UDP glycosyltransferases. For example, the substrate can be natural *Stevia* extract, steviol, steviol-13-O-glucoside, steviol-19-O-glucoside, steviol-1,2-bioside, rubososide, stevioside, rebaudioside A, rebaudioside G or rebaudioside E. The substrate can be a pure compound or a mixture of different compounds. Preferably, the substrate includes a compound selected from the group consisting of rubososide, stevioside, steviol, rebaudioside A, rebaudioside E and combinations thereof.

The method described herein also provides a coupling reaction system in which the recombinant peptides described herein can function in combination with one or more additional enzymes to improve the efficiency or modify the outcome of the overall biosynthesis of steviol glycoside compounds. For example, the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction.

In another embodiment, the method of the subject technology further includes incubating a recombinant UDP-glycosyltransferase with the recombinant sucrose synthase, the substrate, and the recombinant polypeptide described herein. The recombinant UDP-glycosyltransferase can catalyze a different glycosylation reaction than the one catalyzed by the recombinant polypeptide of the subject technology.

Suitable UDP-glycosyltransferase includes any UGT known in the art as capable of catalyzing one or more reactions in the biosynthesis of steviol glycoside compounds, such as UGT85C2, UGT74G1, UGT76G1, or the functional homologs thereof.

Typically, in the in vitro method of the subject technology, UDP or UDP-Glucose is included in the buffer at a concentration of from about 0.2 mM to about 5 mM, preferably from about 0.5 mM to about 2 mM, more preferably from about 0.7 mM to about 1.5 mM. In an embodiment, when a recombinant sucrose synthase is included in the reaction, sucrose is also included in the buffer at a concentration of from about 100 mM to about 500 mM, preferably from about 200 mM to about 400 mM, more preferably from about 250 mM to about 350 mM. In some embodiments, in the in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

In some embodiments, the reaction temperature of the in vitro method is from about 20° C. to about 40° C., suitably from 25° C. to about 37° C., more suitably from 28° C. to about 32° C.

One with skill in the art will recognize that the steviol glycoside composition produced by the method described herein can be further purified and mixed with other steviol glycosides, flavors, or sweeteners to obtain a desired flavor or sweetener composition. For example, a composition enriched with rebaudioside M or Reb I produced as described herein can be mixed with a natural *Stevia* extract containing rebaudioside A as the predominant steviol glycoside, or with other synthetic or natural steviol glycoside products to make a desired sweetener composition. Alternatively, a substantially purified steviol glycoside (e.g., rebaudioside I) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside compositions described herein (including rebaudioside D, rebaudioside A, rebaudioside I, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

One with skill in the art will recognize that the steviol glycoside composition produced by the method described herein can be further purified and mixed with other steviol glycosides, flavors, or sweeteners to obtain a desired flavor or sweetener composition. For example, a composition enriched with rebaudioside I produced as described herein can be mixed with a natural *Stevia* extract containing rebaudioside A as the predominant steviol glycoside, or with other synthetic or natural steviol glycoside products to make a desired sweetener composition. Alternatively, a substantially purified steviol glycoside (e.g., rebaudioside I) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside A, rebaudioside I, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Mutant Enzymes

Based on the crystal structure of UGT76G1, a series of circular permutations and a set of mutations were designed and tested for their function. After activity screening, one version of UGT76G1 circular permutation mutant, CP1, was found to be significantly active. Broadly speaking, CP1 is a variant of UGT76G1 with its domains switched and identified mutation sites. CP1 demonstrated significant activity in terms of glucosylation of the steviol core. When a linker was inserted into the CP1 mutant to generate a second mutant CP2, CP2 was found to show similar activity as the CP1 mutant.

Based on modeling analysis of UGT76G1, mutation sites for the UGT76G1 enzyme were selected and tested for their activities in the bioconversion of Reb A to Reb I. After a series of such mutations, a handful of mutants were identified with the desired enzymatic function with regard to glycosylation activity and ornamentation of the steviol core. Then a genetically modified microbe was developed, which is capable of converting Reb A to Reb I. For example, one UGT76G1 mutant (L200A, referred to herein as the LA mutant) was found to have extremely high enzymatic activity for the bioconversion of Reb A to Reb I. The LA mutant includes one mutation site (L200A) from the UGT76G1 sequence. In some embodiments, the LA mutant comprises the amino acid sequence of SEQ ID NO: 1.

EXAMPLES

Example 1: Enzymatic Activity Screening of UGT Enzymes

Figure 2:
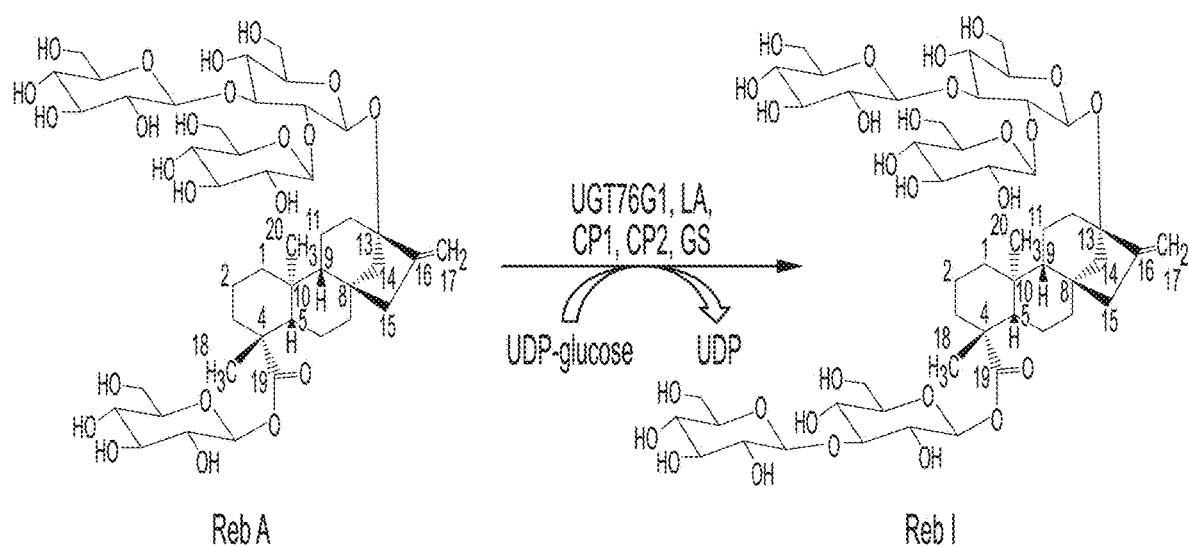
FIG. 2 shows the biosynthesis pathway of Reb I from Reb A.

The majority of the steviol glycosides are formed by several glycosylation reactions of steviol, which typically are catalyzed by the UDP-glycosyltransferases (UGTs) using uridine 5'-diphosphoglucose (UDP-glucose) as a donor of the sugar. In plants, UGTs are a very divergent group of enzymes that transfer a glucose residue from UDP-glucose to steviol. For example, glycosylation of the C-3' of the C-13-O-glucose of stevioside yields rebaudioside A (UGT76G1). In order to produce rebaudioside I (Reb I) from Reb A, the UGT needs to transfer a glucose residue from UDP-glucose to Reb A, glycosylating of the C-3' position of the C-19-O-glucose of Reb A (FIG. 2). In order to identify the specific UGT enzyme for Reb I production from Reb A, UGT76G1 and related mutants were chosen based on protein structure for activity screening.

Full-length DNA fragments of all candidate UGT genes were commercially synthesized. Almost all codons of the cDNA were changed to those preferred for E. coli (Genscript, N.J.). The synthesized DNA was cloned into a bacterial expression vector pETite N-His SUMO Kan Vector (Lucigen).

Each expression construct was transformed into E. coli BL21 (DE3), which was subsequently grown in LB media containing 50 µg/mL kanamycin at 37° C. until reaching an OD600 of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 ug/ml lysozyme, 5 ug/ml DNase I, 20 mM imidazole, 500 mM NaCl, 10% glycerol, and 0.4% Triton X-100). The cells were disrupted by sonication under 4° C., and the cell debris was clarified by centrifugation (18,000×g; 30 min). Supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged beta-glucosidase recombinant polypeptides were eluted by equilibration buffer containing 250 mM imidazole.

The purified candidate UGT recombinant polypeptides were assayed for glycosyltransferase activity by using various steviol glycosides as substrate. Typically, the recombinant polypeptide (20 μg) was tested in a 200 μl in vitro reaction system. The reaction system contains 50 mM potassium phosphate buffer, pH 7.2, 3 mM $MgCl_2$, 1 mg/ml steviol glycoside and 3 mM UDP-glucose. The reaction was performed at 30-37° C. and 50 ul reaction was terminated by adding 200 μL 1-butanol at various time points. The samples were extracted three times with 200 μL 1-butanol. The pooled fraction was dried and dissolved in 100 μL 80% methanol for high-performance liquid chromatography (HPLC) analysis.

HPLC analysis was then performed using a Dionex UPLC ultimate 3000 system (Sunnyvale, Calif.), including a quaternary pump, a temperature-controlled column compartment, an auto sampler and a UV absorbance detector. A Synergi Hydro-RP column (Phenomenex) with guard column was used for the characterization of steviol glycosides in the pooled samples. The detection wavelength used in the HPLC analysis was 210 nm.

After activity screening, several enzymes having UDP-glycosyltransferase activity were identified for Reb I production.

UGT76G1 enzyme can convert Reb A to Reb I. After screening various mutants and variants, a particular variant, LA, which has only one mutation (L200A) compared to the wild type UGT76G1, unexpectedly showed significantly higher activity in converting Reb A to Reb I as described in more details in Example 2.

Example 2: Enzymatic Bioconversion of Reb A to Reb I

Circular permutation analysis is a powerful tool to develop useful or valuable enzymes (PLoS computational Biology, 2012, 8(3) e1002445; BIOINFORMATICS, 2015, (3)). Based on the crystal structure of UGT76G1, a series of circular permutations were designed. After performing activity screening, one version of circular permutation ("CP1") was found to have higher activity for Reb I production compared to WT UGT76G1. A linker (YKDDSGYSSSYAAAAGM) was inserted between the C-terminal and the N terminal of CP1 to generate a second mutant ("CP2"), which also has higher activity than WT UGT76G1 for Reb I production.

Based on modeling analysis of UGT76G1, mutation sites were selected to enhance enzymatic activity. After enzymatic activity screening of the various mutants generated, it was unexpectedly found that one mutant, LA (an L200A mutant of UGT76G1), showed a significant increase in its enzymatic activity in converting Reb A to Reb I, especially when compared to the wild type UGT76G1.

To confirm the conversion of rebaudioside A to rebaudioside I in vitro, the selected UGT enzymes were assayed using Reb A as the steviol glycoside substrate. The reaction system contained 50 mM potassium phosphate buffer (pH 7.2), 3 mM $MgCl_2$, 1 mg/ml stevioside, 3 mM UDP-glucose, and enzyme (20 ug/200 ul reaction). The reaction was performed at 37° C. and terminated by adding 1-butanol. The samples were extracted three times with 1-butanol. The pooled fraction was dried and dissolved in 80% methanol for high-performance liquid chromatography (HPLC) analysis. HPLC analysis was performed as above description.

Figure 3:
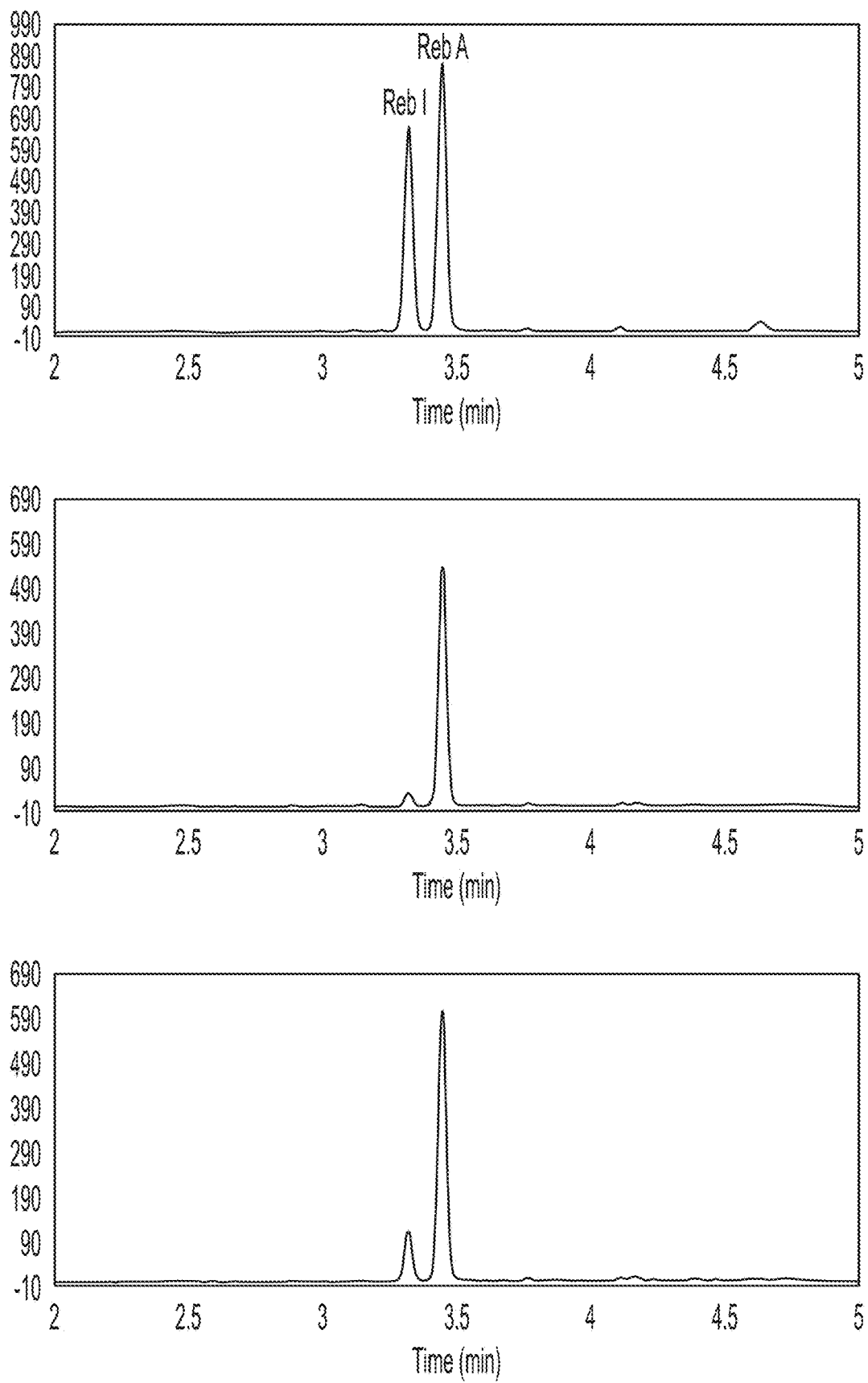
FIG. 3 shows the in vitro production of Reb I from Reb A catalyzed by selected UGTs after 6 hours of incubation. Panel A shows the standards of rebaudioside A (Reb A) and rabaudioside I (Reb I). Panels B-F, respectively, show the amount of Reb I enzymatically produced from Reb A by UGT76G1 (B), CP1 (C), CP2 (D), LA (E) and UGT76G1-AtSUS1 fusion enzyme (GS) (F).
Figure 3:
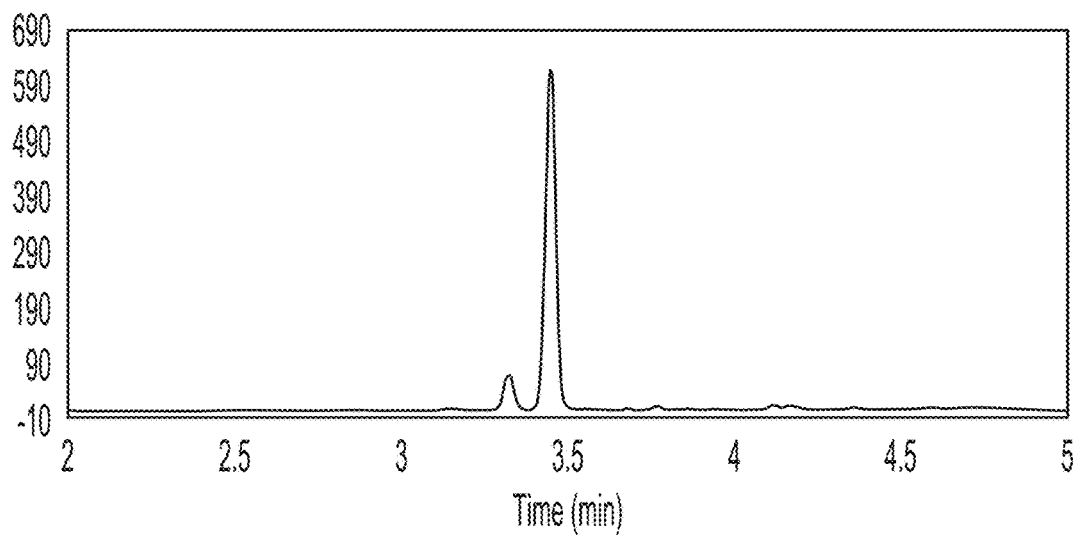
Figure 3:
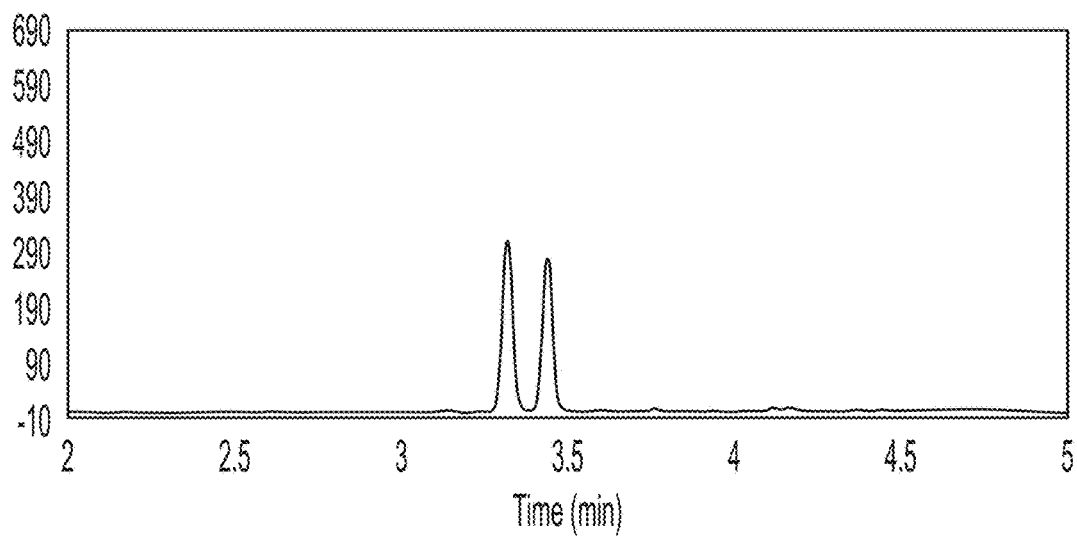
Figure 3:
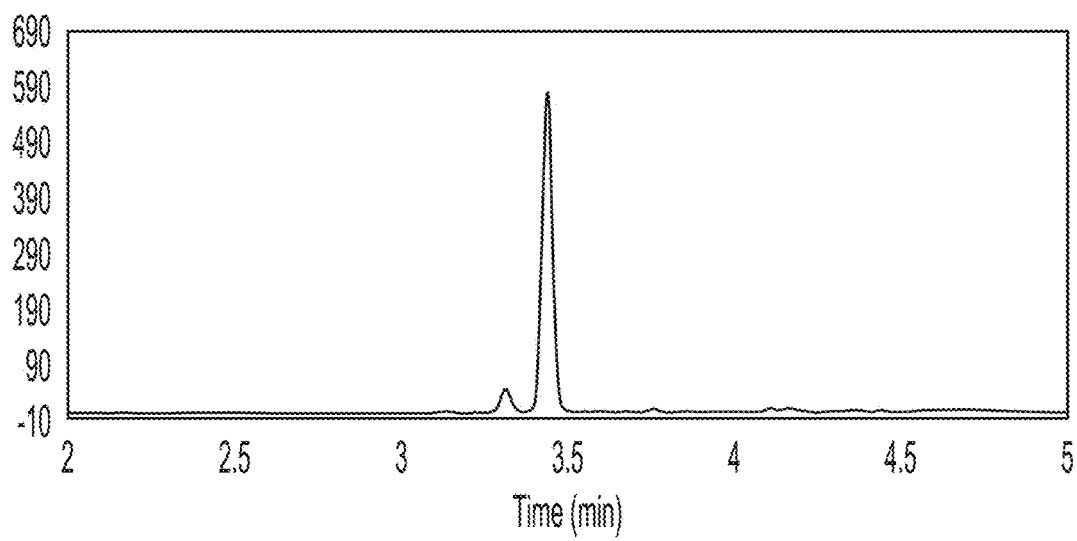

As shown in FIG. 3, UGT76G1 can convert Reb A to Reb I (FIG. 3, panel B). Both CP1 (FIG. 3, panel C) and CP2 (FIG. 3, panel D) mutants have higher enzymatic activity than UGT76G1. CP2 has lower activity than CP1 indicating that the selected linker between the N-terminal and C-terminal affects the enzymatic activity. In order to identify the mutants having high enzymatic activity, several site mutants were generated based on UGT76G1 crystal structure. After activity screening, mutants that have higher activity than UGT76G1 were found. The LA mutant (L200A) has the highest activity among all the tested mutants. As shown in FIG. 3, panel E, the peaks corresponding to Reb I and Reb A, respectively, show that more than 50% of the Reb A was consumed and converted to Reb I when LA was used. By comparison, when any of UGT76G1, CP1 and CP2 was used, less than 15% of Reb A was converted to Reb I (FIG. 3, panels B-D). The UGT76G1-AtSUS1 fusion enzyme (GS) also showed higher activity for bioconversion of Reb A to Reb I (FIG. 3, panel F) compared to UGT76G1, although not as significant as LA, CP1 or CP2.

In a coupling system in which both a UGT enzyme and a sucrose synthase (SUS) are present, UDP-glucose can be regenerated from UDP and sucrose, which allows for omitting the addition of extra UDP-glucose to the reaction mixture. Suitable sucrose synthases (SUS) can be for example, an *Arabidopsis* sucrose synthase 1; an *Arabidopsis* sucrose synthase 3; and a *Vigna* radiate sucrose synthase.

Figure 4:
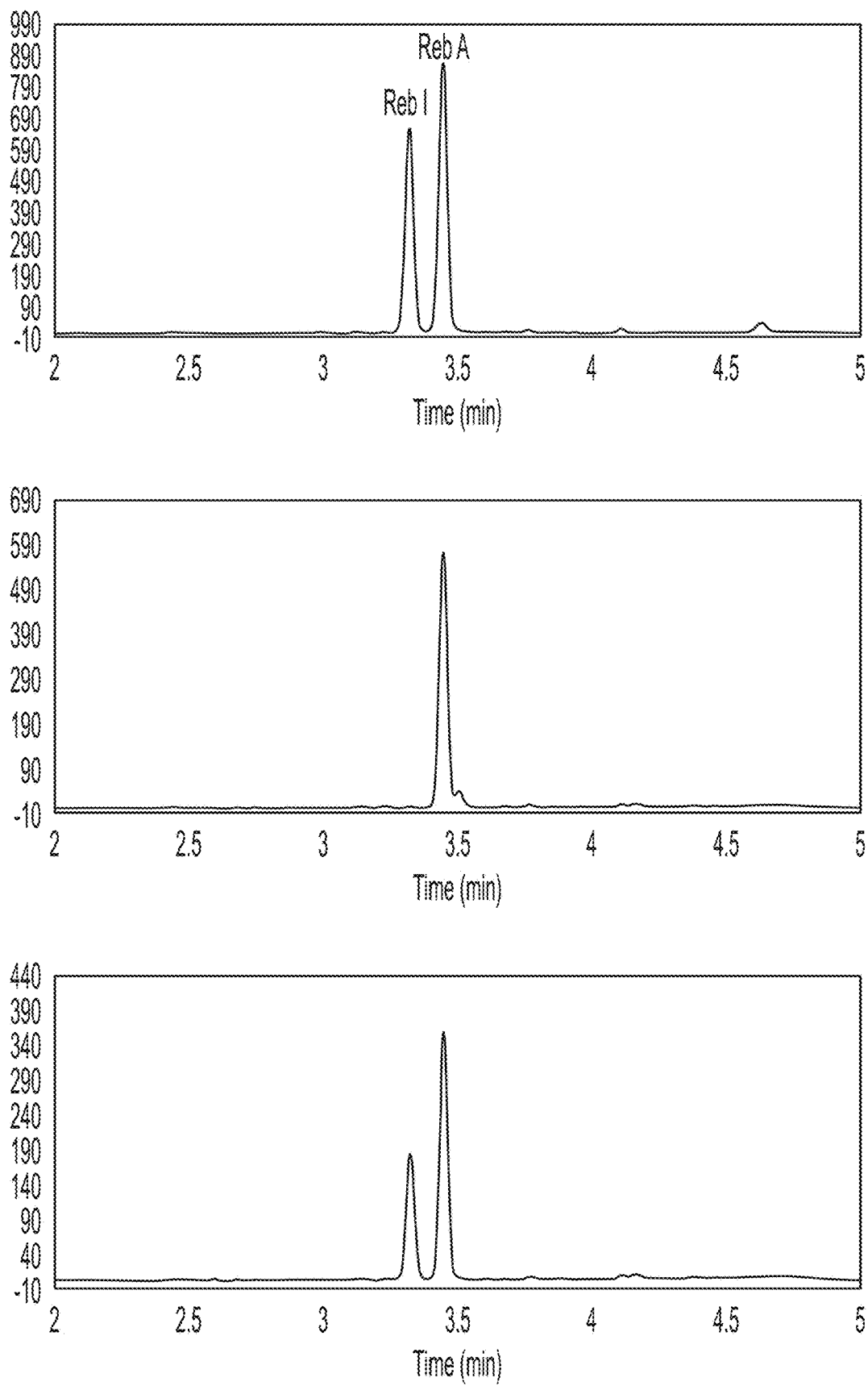
FIG. 4 shows the in vitro production of Reb I from Reb A catalyzed by UGT76G1, a coupling system in which both UGT76G1 and AtSUS1 are present, and a UGT76G1-AtSUS1 fusion enzyme ("GS"), with the addition of UDP and sucrose. Panel A shows the standards of rebaudioside I (Reb I) and rebaudioside A (Reb A). Panels B-D, respectively, show the amount of Reb I converted from Reb A in an enzymatic reaction catalyzed by UGT76G1 (B), a coupling system in which both UGT76G1 and AtSUS1 are present (C), and a UGT76G1-AtSUS1 fusion enzyme (GS) (D).
Figure 4:
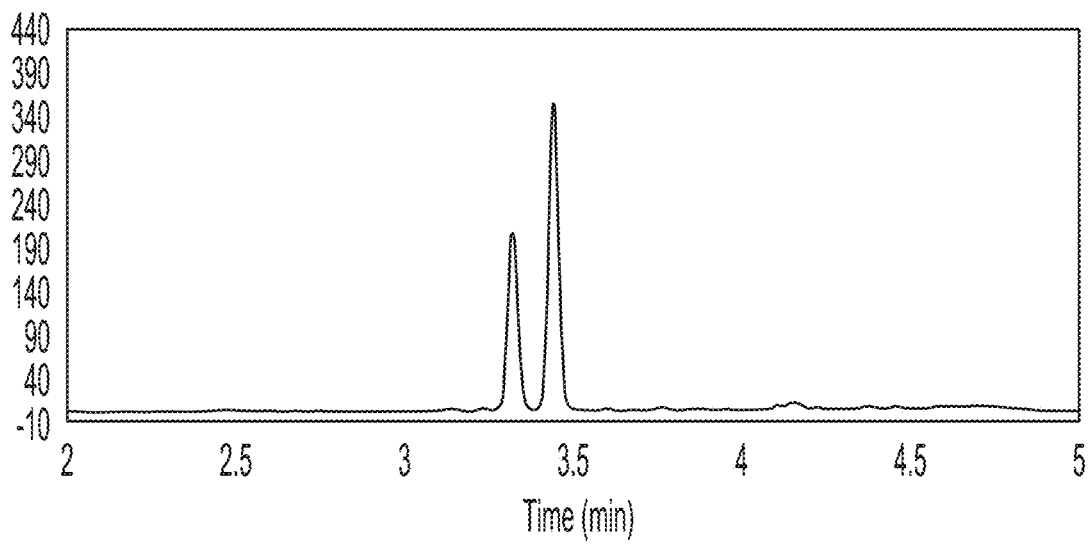

In another aspect, UDP-glycosyltransferase fusion enzyme can be used in the methods. A particularly suitable UDP-glycosyltransferase fusion enzyme can be a UGT-SUS fusion enzyme. The UDP-glycosyltransferase can be a UDP-glycosyltransferase fusion enzyme that includes a UDP-glycosyltransferase domain coupled to a sucrose synthase domain. In particular, the UDP-glycosyltransferase fusion enzyme includes a UDP-glycosyltransferase domain coupled to a sucrose synthase domain. Additionally, the UGT-SUS fusion enzyme has sucrose synthase activity, and thus, can regenerate UDP-glucose from UDP and sucrose. A particularly suitable UGT-SUS fusion enzyme can be, for example, a UGT76G1-AtSUS1 fusion enzyme (named as: "GS"). GS fusion enzyme can convert Reb A to Reb I in addition of UDP and sucrose (FIG. 4). As shown in FIG. 4, UGT76G1 cannot convert Reb A to Reb I in UDP addition (FIG. 4, panel B). However, both of GS fusion enzyme (FIG. 4, panel D) and combination of UGT76G1 and AtSUS1 enzyme system (FIG. 4 C) can produce Reb I from Reb A indicating the UDPG regeneration by AtSUS1 sucrose synthase. It was also found that GS fusion enzyme has higher enzymatic activity than the combination of UGT76G1 and AtSUS1 enzyme in the same reaction system. Sucrose synthases (SUS) catalyze the conversion of the UDP to UDP-glucose in the presence of sucrose. Thus, for a glycosylation reaction utilizing UDP-glucose (such as those catalyzed by the UGTs), SUS can be used to re-generate UDP-glucose from UDP, enhancing the efficiency of such reaction.

Example 3: NMR Analysis the Structure of Produced Reb I

The produced Reb I compound was purified by semi preparative chromatography as described above.

The molecular formula of Reb I has been deduced as $C_{50}H_{80}O_{28}$ on the basis of its positive High Resolution Mass Spectrum (HRMS) which showed an adduct ions corresponding to [M+NH$_4$]$^+$ and [M+Na]$^+$ at m/z 1146.5281 and 1151.4839 respectively, and this composition was supported by the $^{13}$C NMR spectral data. The $^1$H NMR spectrum of Reb I showed the presence of two methyl singlets at δ 1.22, and 1.26; nine methylene and two methine protons between δ 0.75-2.59; and two singlets corresponding to an exocyclic double bond at δ 5.01 and 5.65; similar to the ent-kaurane diterpenoids isolated earlier from *S. rebaudiana*. The basic skeleton of ent-kaurane diterpenoids was supported by the key TOCSY (H-1/H-2; H-2/H-3; H-5/H-6; H-6/H-7; H-9/H-11; H-11/H-12) and HMBC (H-1/C-2, C-10; H-3/C-1, C-2, C-4, C-5, C-18, C-19; H-5/C-4, C-6, C-7, C-9, C-10, C-18, C-19, C-20; H-9/C-8, C-10, C-11, C-12, C-14, C-15; H-14/C-8, C-9, C-13, C-15, C-16 and H-17/C-13, C-15, C-16) correlations.

Further, the $^1$H NMR spectrum of Reb I showed anomeric protons as doublets at δ 5.03, 5.24, 5.34, 5.53, and 6.12 suggesting the presence of five sugar units in its structure. Acid hydrolysis of Reb I with 5% H$_2$SO$_4$ afforded D-glucose which was identified by direct comparison with authentic sample by TLC suggested the presence of six glucopyranosyl moieties in its molecular structure. The configuration of D-glucose was identified by preparing its corresponding thiocarbamoyl-thiazolidine carboxylate derivative with L-cysteine methyl ester and O-tolyl isothiocyanate, and in comparison, of its retention time with the standard sugars as described in the literature comparison. Enzymatic hydrolysis of Reb I furnished an aglycone which was identified as steviol by comparison of $^1$H NMR and co-TLC with standard compound. The $^1$H and $^{13}$C NMR values for compound Reb I were assigned on the basis of COSY, TOCSY, HMQC, HMBC and ROESY data.

TABLE 2

$^1$H and $^{13}$C NMR spectral data (chemical shifts and coupling constants) for produced Rebaudioside I [a-c].

| Position | $^1$H NMR | $^{13}$C NMR |
|---|---|---|
| 1 | 0.75 (dt, J = 3.1, 12.8, 1H), 1.77 (m, 1H) | 41.0 |
| 2 | 1.45 (m, 1H), 2.20 (m, 1H) | 19.7 |
| 3 | 1.00 (m, 1H), 2.32 d (12.8) | 38.8 |
| 4 |  | 44.6 |
| 5 | 1.02 (d, J = 12.8, 1H) | 57.5 |
| 6 | 1.89 (m, 1H), 2.28 (m, 1H) | 22.5 |
| 7 | 1.33 (m, 1H) | 42.0 |
| 8 |  | 42.6 |
| 9 | 0.88 (d, J = 7.6, 1H) | 54.4 |
| 10 |  | 40.1 |
| 11 | 1.64 (m, 1H), 1.72 (m, 1H) | 20.8 |
| 12 | 1.95 (m, 1H), 2.33 (m, 1H) | 37.6 |
| 13 |  | 86.9 |
| 14 | 1.76 (m, 1H), 2.59 (d, J = 11.2, 1H) | 44.3 |
| 15 | 2.06 (br q, J = 8.5, 1H) | 48.0 |
| 16 |  | 154.3 |
| 17 | 5.01 (s, 1H), 5.65 (s, 1H) | 105.0 |
| 18 | 1.22 (s, 3H) | 28.7 |
| 19 |  | 177.2 |
| 20 | 1.26 (s, 3H) | 16.0 |
| 1' | 6.12 (d, J = 8.1, 1H) | 95.6 |
| 2' | 4.16 (m, 1H) | 72.5 |
| 3' | 4.24 (m, 1H) | 89.8 |
| 4' | 4.21 (m, 1H) | 69.6 |
| 5' | 3.90 (m, 1H) | 78.3 |
| 6' | 4.25 (m, 1H), 4.39 (m, 1H) | 62.6 |
| 1" | 5.03 (d, J = 7.8, 1H) | 98.3 |
| 2" | 4.30 (m, 1H) | 80.9 |
| 3" | 4.16 (m, 1H) | 88.1 |
| 4" | 4.08 (m, 1H) | 70.4 |
| 5" | 3.77 (m, 1H) | 77.9 |
| 6" | 4.18 (m, 1H), 4.48 (m, 1H) | 62.7 |
| 1''' | 5.53 (d, J = 7.8, 1H) | 104.9 |
| 2''' | 4.18 (m, 1H) | 76.5 |
| 3''' | 4.29 (m, 1H) | 78.5 |
| 4''' | 4.23 (m, 1H) | 72.8 |
| 5''' | 3.94 (m, 1H) | 77.8 |
| 6''' | 4.36 (m, 1H), 4.54 (m, 1H) | 62.9 |
| 1'''' | 5.34 (d, J = 7.8, 1H) | 105.0 |
| 2'''' | 3.98 (m, 1H) | 75.6 |
| 3'''' | 4.14 (m, 1H) | 78.8 |
| 4'''' | 4.08 (m, 1H) | 71.8 |
| 5'''' | 4.12 (m, 1H) | 78.5 |
| 6'''' | 4.20 (m, 1H), 4.52 (m, 1H) | 62.0 |
| 1''''' | 5.24 (d, J = 7.8, 1H) | 105.4 |
| 2''''' | 4.06 (m, 1H) | 75.6 |
| 3''''' | 4.31 (m, 1H) | 78.8 |
| 4''''' | 4.11 (m, 1H) | 71.9 |
| 5''''' | 4.07 (m, 1H) | 78.9 |
| 6''''' | 4.32 (m, 1H), 4.52 (m, 1H) | 63.4 |

[a] assignments made on the basis of COSY, TOCSY, HMQC, HMBC and ROESY correlations;
[b] Chemical shift values are in δ (ppm);
[c] Coupling constants are in Hz.

Figure 5:
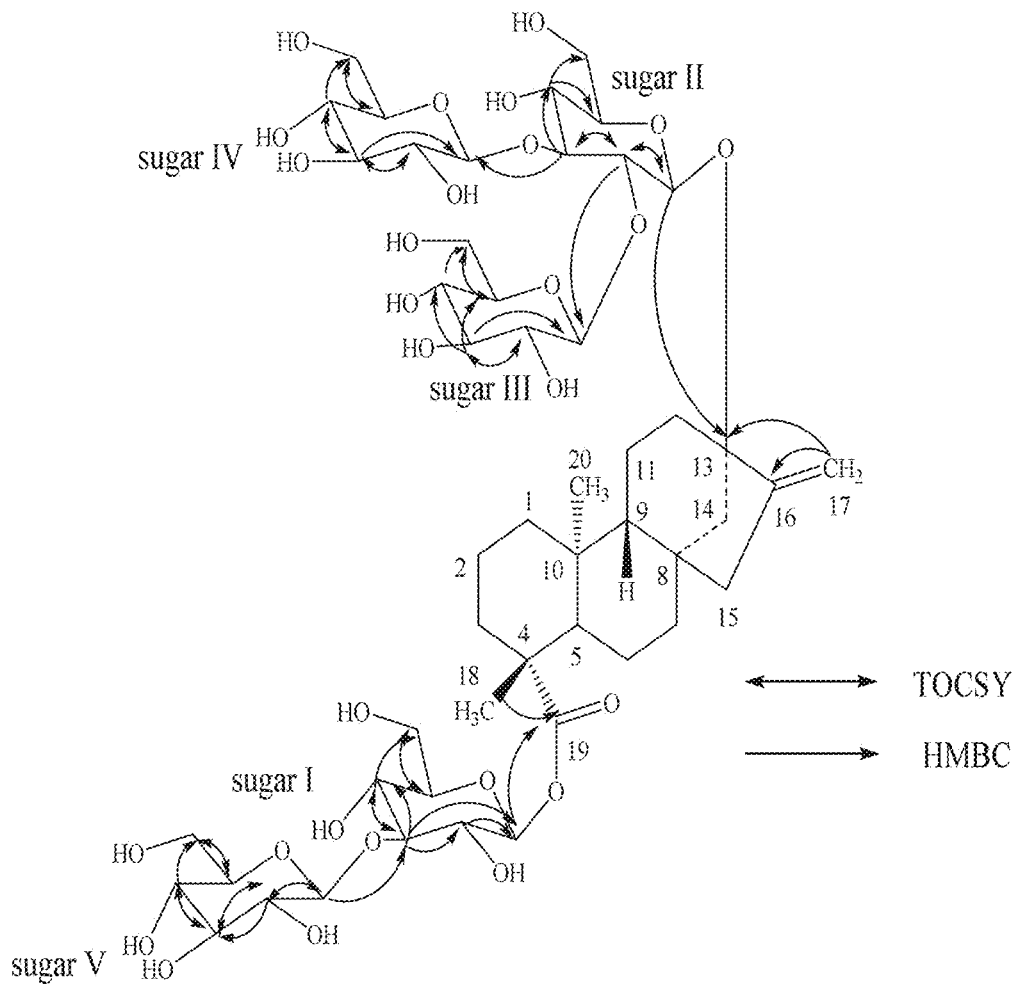
FIG. 5 shows the key TOCSY and HMBC correlations of rebaudioside I.

A close study of the $^1$H and $^{13}$C NMR values of Reb I together with enzymatic and acid hydrolysis experiments suggested that compound Reb I is also a steviol glycoside with three glucosyl moieties residues that are attached at the C-13 hydroxyl as a 2,3-branched glucotriosyl substituent and another glucosyl moiety in the form of an ester at C-19 position leaving the identification of additional glucosyl unit. The downfield shift for both the $^1$H and $^{13}$C chemical shifts at 3'-position of sugar I suggested the additional β-D-glucosyl moiety at this position which was supported by the key HMBC correlations: H-1'/C-19, C-2'; H-2'/C-1', C-3' and H-3'/C-1', C-2' and C-4'. The large coupling constants observed for the five anomeric protons at δ 5.03 (d, J=7.8 Hz), 5.24 (d, J=7.8 Hz), 5.34 (d, J=7.8 Hz), 5.53 (d, J=7.8 Hz) and 6.12 (d, J=8.1 Hz), suggested their β-orientation as reported for steviol glycosides. The structure of Reb I was further supported by the key TOCSY, and HMBC correlations as shown in FIG. 5.

Based on the results from chemical and spectral studies, Reb I was assigned as 13-[(2-O-β-D-glucopyranosyl-3-O-β-D-glucopyranosyl-β-D-glucopyranosyl)oxy] ent-kaur-16-en-19-oic acid-(3-O-β-D-glucopyranosyl-β-D-glucopyranosyl) ester and its spectral data are in consistent with the structural data of Reabudioside I reported in the literature.

A solution of produced Reb I (3 mg) in MeOH (10 ml) was added 3 ml of 5% H$_2$SO$_4$ and the mixture was refluxed for 16 hours. The reaction mixture was then neutralized with saturated sodium carbonate and extracted with ethyl acetate (EtOAc) (2×25 ml) to give an aqueous fraction containing sugars and an EtOAc fraction containing the aglycone part. The aqueous phase was concentrated and compared with standard sugars using the TLC systems EtOAc/n-butanol/water (2:7:1) and CH$_2$Cl$_2$/MeOH/water (10:6:1) [6-8]; the sugars were identified as D-glucose.

Produced Reb I (500 μg) was hydrolyzed with 0.5 M HCl (0.5 mL) for 1.5 h. After cooling, the mixture was passed through an Amberlite IRA400 column and the eluate was lyophilized. The residue was dissolved in pyridine (0.25 mL) and heated with L-cysteine methyl ester HCl (2.5 mg) at 60° C. for 1.5 h, and then O-tolyl isothiocyanate (12.5 uL) was added to the mixture and heated at 60° C. for an additional 1.5 h. HPLC analysis of the reaction mixture was performed by a Phenomenex Luna column [C18, 150×4.6 mm (5 u)] using the mobile phase 25% acetonitrile-0.2% TFA water, 1 mL/min under UV detection at 250 nm. The sugar was identified as D-glucose (tR, 12.64) [authentic samples, D-glucose (tR, 12.54) and L-glucose (tR, 11.42 min)] [9].

Produced Reb I (1 mg) was dissolved in 2.5 ml of 0.1 M sodium acetate buffer by maintaining pH at 4.5 and 50 μL of crude pectinase from *Aspergillus niger* (Sigma-Aldrich) was added. The mixture was stirred at 50° C. for 48 hr and the product precipitated out during the reaction was filtered and then crystallized. The resulting product obtained was identified as steviol by comparison of their $^1$H NMR spectral data and co-TLC.

The complete $^1$H and $^{13}$C NMR spectral data for 13-[(2-O-β-D-glucopyranosyl-3-O-β-D-glucopyranosyl-β-D-glucopyranosyl)oxy] ent-kaur-16-en-19-oic acid-(3-O-β-D-glucopyranosyl-β-D-glucopyranosyl) ester (Rebaudioside I) produced by enzymatic bioconversion has been assigned on the basis of extensive 1D and 2D NMR as well as high resolution mass spectral data. The structure of Rebaudioside I was further supported by acid and enzymatic hydrolysis studies.

```
Sequences of Interest
UGT76G1 L200A mutant (LA): Amino Acid Sequence:
                                                        (SEQ ID NO: 1)
MENKTETTVRRRRRIILFPVPFQGHINPILQLANVLYSKGFSITIFHTNFNKPKTSNYPHF

TFRFILDNDPQDERISNLPTHGPLAGMRIPIINEHGADELRRELELLMLASEEDEEVSCLI

TDALWYFAQSVADSLNLRRLVLMTSSLFNFHAHVSLPQFDELGYLDPDDKTRLEEQA

SGFPMLKVKDIKSAYSNWQIAKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

VDSKQSFLWVVRPGFVKGSTWVEPLPDGFLGERGRIVKWVPQQEVLAHGAIGAFWT

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSL

UGT76G1 L200A mutant (LA): DNA Sequence:
                                                        (SEQ ID NO: 2)
ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTGCGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

GTTCTTAATTCCACTACCCAAGCACCTTACTGCAAGTAGCAGTTCCCTCCTAGATC

ATGACCGAACCGTGTTTCAGTGGCTGGATCAGCAACCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTTCTGATTTTGGGCTTGACCAGCCTCTAAACGCTCGCTATATGTCT

GATGTGTTGAAGGTTGGCGTGTACCTGGAGAATGGTTGGGAAAGGGGGGAAATTG
```

-continued

```
CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

TATGAATCCCTAGAATCCTTGGTAAGCTATATATCTTCGTTATAA
```

UGT76G1 CP1 mutant (CP1): Amino Acid Sequence:
(SEQ ID NO: 3)
```
MNWQILKEILGKMIKQTKASSGVIWNSFKELEESELETVIREIPAPSFLIPLPKHLTASSS

SLLDHDRTVFQWLDQQPPSSVLYVSFGSTSEVDEKDFLEIARGLVDSKQSFLWVVRPG

FVKGSTWVEPLPDGFLGERGRIVKWVPQQEVLAHGAIGAFWTHSGWNSTLESVCEGV

PMIFSDFGLDQPLNARYMSDVLKVGVYLENGWERGEIANAIRRVMVDEEGEYIRQNA

RVLKQKADVSLMKGGSSYESLESLVSYISSLENKTETTVRRRRRIILFPVPFQGHINPIL

QLANVLYSKGFSITIFHTNFNKPKTSNYPHFTFRFILDNDPQDERISNLPTHGPLAGMRI

PIINEHGADELRRELELLMLASEEDEEVSCLITDALWYFAQSVADSLNLRRLVLMTSSL

FNFHAHVSLPQFDELGYLDPDDKTRLEEQASGFPMLKVKDIKSAYS
```

UGT76G1 CP1 mutant (CP1): DNA Sequence:
(SEQ ID NO: 4)
```
ATGAACTGGCAAATCCTGAAAGAAATCCTGGGTAAAATGATCAAACAAACCAAAG

CGTCGTCGGGCGTTATCTGGAACTCCTTCAAAGAACTGGAAGAATCAGAACTGGA

AACCGTTATTCGCGAAATCCCGGCTCCGTCGTTCCTGATTCCGCTGCCGAAACATC

TGACCGCGAGCAGCAGCAGCCTGCTGGATCACGACCGTACGGTCTTTCAGTGGCT

GGATCAGCAACCGCCGTCATCGGTGCTGTATGTTTCATTCGGTAGCACCTCTGAAG

TCGATGAAAAAGACTTTCTGGAAATCGCTCGCGGCCTGGTGGATAGTAAACAGTC

CTTCCTGTGGGTGGTTCGTCCGGGTTTTGTGAAAGGCAGCACGTGGGTTGAACCGC

TGCCGGATGGCTTCCTGGGTGAACGCGGCCGTATTGTCAAATGGGTGCCGCAGCA

AGAAGTGCTGGCACATGGTGCTATCGGCGCGTTTTGGACCCACTCTGGTTGGAACA

GTACGCTGGAATCCGTTTGCGAAGGTGTCCCGATGATTTTCAGCGATTTTGGCCTG

GACCAGCCGCTGAATGCCCGCTATATGTCTGATGTTCTGAAAGTCGGTGTGTACCT

GGAAAACGGTTGGGAACGTGGCGAAATTGCGAATGCCATCCGTCGCGTTATGGTC

GATGAAGAAGGCGAATACATTCGCCAGAACGCTCGTGTCCTGAAACAAAAAGCGG

ACGTGAGCCTGATGAAAGGCGGTAGCTCTTATGAATCACTGGAATCGCTGGTTAG

CTACATCAGTTCCCTGGAAAATAAAACCGAAACCACGGTGCGTCGCCGTCGCCGT

ATTATCCTGTTCCCGGTTCCGTTTCAGGGTCATATTAACCCGATCCTGCAACTGGC

GAATGTTCTGTATTCAAAAGGCTTTTCGATCACCATCTTCCATACGAACTTCAACA

AACCGAAAACCAGTAACTACCCGCACTTTACGTTCCGCTTTATTCTGGATAACGAC

CCGCAGGATGAACGTATCTCCAATCTGCCGACCCACGGCCCGCTGGCCGGTATGC

GCATTCCGATTATCAATGAACACGGTGCAGATGAACTGCGCCGTGAACTGGAACT

GCTGATGCTGGCCAGTGAAGAAGATGAAGAAGTGTCCTGTCTGATCACCGACGCA

CTGTGGTATTTCGCCCAGAGCGTTGCAGATTCTCTGAACCTGCGCCGTCTGGTCCT

GATGACGTCATCGCTGTTCAATTTTCATGCGCACGTTTCTCTGCCGCAATTTGATGA

ACTGGGCTACCTGGACCCGGATGACAAAACCCGTCTGGAAGAACAAGCCAGTGGT

TTTCCGATGCTGAAAGTCAAAGACATTAAATCCGCCTATTCGTAA
```

UGT76G1 CP2 mutant (CP2): Amino Acid Sequence:
(SEQ ID NO: 5)
```
MNWQILKEILGKMIKQTKASSGVIWNSFKELEESELETVIREIPAPSFLIPLPKHLTASSS

SLLDHDRTVFQWLDQQPPSSVLYVSFGSTSEVDEKDFLEIARGLVDSKQSFLWVVRPG
```

-continued

FVKGSTWVEPLPDGFLGERGRIVKWVPQQEVLAHGAIGAFWTHSGWNSTLESVCEGV

PMIFSDFGLDQPLNARYMSDVLKVGVYLENGWERGEIANAIRRVMVDEEGEYIRQNA

RVLKQKADVSLMKGGSSYESLESLVSYISSLYKDDSGYSSSYAAAAGMENKTETTVRRRR

RIILFPVPFQGHINPILQLANVLYSKGFSITIFHTNFNKPKTSNYPHFTFRFILDNDPQ

DERISNLPTHGPLAGMRIPIINEHGADELRRELELLMLASEEDEEVSCLITDALWYFAQS

VADSLNLRRLVLMTSSLFNFHAHVSLPQFDELGYLDPDDKTRLEEQASGFPMLKVKDI

KSAYS

UGT76G1 CP2 mutant (CP2): DNA Sequence:
(SEQ ID NO: 6)
ATGAACTGGCAAATCCTGAAAGAAATCCTGGGTAAAATGATCAAACAAACCAAAG

CGTCGTCGGGCGTTATCTGGAACTCCTTCAAAGAACTGGAAGAATCAGAACTGGA

AACCGTTATTCGCGAAATCCCGGCTCCGTCGTTCCTGATTCCGCTGCCGAAACATC

TGACCGCGAGCAGCAGCAGCCTGCTGGATCACGACCGTACGGTCTTTCAGTGGCT

GGATCAGCAACCGCCGTCATCGGTGCTGTATGTTTCATTCGGTAGCACCTCTGAAG

TCGATGAAAAAGACTTTCTGGAAATCGCTCGCGGCCTGGTGGATAGTAAACAGTC

CTTCCTGTGGGTGGTTCGTCCGGGTTTTGTGAAAGGCAGCACGTGGGTTGAACCGC

TGCCGGATGGCTTCCTGGGTGAACGCGGCCGTATTGTCAAATGGGTGCCGCAGCA

AGAAGTGCTGGCACATGGTGCTATCGGCGCGTTTTGGACCCACTCTGGTTGGAACA

GTACGCTGGAATCCGTTTGCGAAGGTGTCCCGATGATTTTCAGCGATTTTGGCCTG

GACCAGCCGCTGAATGCCCGCTATATGTCTGATGTTCTGAAAGTCGGTGTGTACCT

GGAAAACGGTTGGGAACGTGGCGAAATTGCGAATGCCATCCGTCGCGTTATGGTC

GATGAAGAAGGCGAATACATTCGCCAGAACGCTCGTGTCCTGAAACAAAAAGCGG

ACGTGAGCCTGATGAAAGGCGGTAGCTCTTATGAATCACTGGAATCGCTGGTTAG

CTACATCAGTTCCCTGTACAAAGATGACAGCGGTTATAGCAGCAGCTATGCGGCG

GCGGCGGGTATGGAAAATAAAACCGAAACCACGGTGCGTCGCCGTCGCCGTATTA

TCCTGTTCCCGGTTCCGTTTCAGGGTCATATTAACCCGATCCTGCAACTGGCGAAT

GTTCTGTATTCAAAAGGCTTTTCGATCACCATCTTCCATACGAACTTCAACAAACC

GAAAACCAGTAACTACCCGCACTTTACGTTCCGCTTTATTCTGGATAACGACCCGC

AGGATGAACGTATCTCCAATCTGCCGACCCACGGCCCGCTGGCCGGTATGCGCATT

CCGATTATCAATGAACACGGTGCAGATGAACTGCGCCGTGAACTGGAACTGCTGA

TGCTGGCCAGTGAAGAAGATGAAGAAGTGTCCTGTCTGATCACCGACGCACTGTG

GTATTTCGCCCAGAGCGTTGCAGATTCTCTGAACCTGCGCCGTCTGGTCCTGATGA

CGTCATCGCTGTTCAATTTTCATGCGCACGTTTCTCTGCCGCAATTTGATGAACTGG

GCTACCTGGACCCGGATGACAAAACCCGTCTGGAAGAACAAGCCAGTGGTTTTCC

GATGCTGAAAGTCAAAGACATTAAATCCGCCTATTCGTAA

UGT76G1-AtSUS1 fusion enzyme (GS): Amino Acid Sequence:
(SEQ ID NO: 7)
MENKTETTVRRRRRIILFPVPFQGHINPILQLANVLYSKGFSITIFHTNFNKPKTSNYP

HFTFRFILDNDPQDERISNLPTHGPLAGMRIPIINEHGADELRRELELLMLASEEDEEV

SCLITDALWYFAQSVADSLNLRRLVLMTSSLFNFHAHVSLPQFDELGYLDPDDKTRLEEQA

SGFPMLKVKDIKSAYSNWQILKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

VDSKQSFLWVVRPGFVKGSTWVEPLPDGFLGERGRIVKWVPQQEVLAHGAIGAFWT

-continued

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSLGSGANAERMITR

VHSQRERLNETLVSERNEVLALLSRVEAKGKGILQQNQIIAEFEALPEQTRKKLEGGPF

FDLLKSTQEAIVLPPWVALAVRPRPGVWEYLRVNLHALVVEELQPAEFLHFKEELVD

GVKNGNFTLELDFEPFNASIPRPTLHKYIGNGVDFLNRHLSAKLFHDKESLLPLLKFLR

LHSHQGKNLMLSEKIQNLNTLQHTLRKAEEYLAELKSETLYEEFEAKFEEIGLERGWG

DNAERVLDMIRLLLDLLEAPDPCTLETFLGRVPMVFNVVILSPHGYFAQDNVLGYPDT

GGQVVYILDQVRALEIEMLQRIKQQGLNIKPRILILTRLLPDAVGTTCGERLERVYDSE

YCDILRVPFRTEKGIVRKWISRFEVWPYLETYTEDAAVELSKELNGKPDLIIGNYSDGN

LVASLLAHKLGVTQCTIAHALEKTKYPDSDIYWKKLDDKYHFSCQFTADIFAMNHTD

FIITSTFQEIAGSKETVGQYESHTAFTLPGLYRVVHGIDVFDPKFNIVSPGADMSIYFPYT

EEKRRLTKFHSEIEELLYSDVENKEHLCVLKDKKKPILFTMARLDRVKNLSGLVEWYG

KNTRLRELANLVVVGGDRRKESKDNEEKAEMKKMYDLIEEYKLNGQFRWISSQMDR

VRNGELYRYICDTKGAFVQPALYEAFGLTVVEAMTCGLPTFATCKGGPAEIIVHGKSG

FHIDPYHGDQAADTLADFFTKCKEDPSHWDEISKGGLQRIEEKYTWQIYSQRLLT LTG

VYGFWKHVSNLDRLEARRYLEMFYALKYRPLAQAVPLAQDDWT

UGT76G1-AtSUS1 fusion enzyme (GS): DNA Sequence:
(SEQ ID NO: 8)
ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTCTGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

GTTCTTAATTCCACTACCCAAGCACCTTACTGCAAGTAGCAGTTCCCTCCTAGATC

ATGACCGAACCGTGTTTCAGTGGCTGGATCAGCAACCCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTTCTGATTTTGGGCTTGACCAGCCTCTAAACGCTCGCTATATGTCT

GATGTGTTGAAGGTTGGCGTGTACCTGGAGAATGGTTGGGAAAGGGGGGAAATTG

CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

-continued

```
TATGAATCCCTAGAATCCTTGGTAAGCTATATATCTTCGTTAGGTTCTGGTGCAAA
CGCTGAACGTATGATAACGCGCGTCCACAGCCAACGTGAGCGTTTGAACGAAACG
CTTGTTTCTGAGAGAAACGAAGTCCTTGCCTTGCTTTCCAGGGTTGAAGCCAAAGG
TAAAGGTATTTTACAACAAAACCAGATCATTGCTGAATTCGAAGCTTTGCCTGAAC
AAACCCGGAAGAAACTTGAAGGTGGTCCTTTCTTTGACCTTCTCAAATCCACTCAG
GAAGCAATTGTGTTGCCACCATGGGTTGCTCTAGCTGTGAGGCCAAGGCCTGGTGT
TTGGGAATACTTACGAGTCAATCTCCATGCTCTTGTCGTTGAAGAACTCCAACCTG
CTGAGTTTCTTCATTTCAAGGAAGAACTCGTTGATGGAGTTAAGAATGGTAATTTC
ACTCTTGAGCTTGATTTCGAGCCATTCAATGCGTCTATCCCTCGTCCAACACTCCAC
AAATACATTGGAAATGGTGTTGACTTCCTTAACCGTCATTTATCGGCTAAGCTCTT
CCATGACAAGGAGAGTTTGCTTCCATTGCTTAAGTTCCTTCGTCTTCACAGCCACC
AGGGCAAGAACCTGATGTTGAGCGAGAAGATTCAGAACCTCAACACTCTGCAACA
CACCTTGAGGAAAGCAGAAGAGTATCTAGCAGAGCTTAAGTCCGAAACACTGTAT
GAAGAGTTTGAGGCCAAGTTTGAGGAGATTGGTCTTGAGAGGGGATGGGGAGACA
ATGCAGAGCGTGTCCTTGACATGATACGTCTTCTTTTGGACCTTCTTGAGGCGCCT
GATCCTTGCACTCTTGAGACTTTTCTTGGAAGAGTACCAATGGTGTTCAACGTTGT
GATCCTCTCTCCACATGGTTACTTTGCTCAGGACAATGTTCTTGGTTACCCTGACAC
TGGTGGACAGGTTGTTTACATTCTTGATCAAGTTCGTGCTCTGGAGATAGAGATGC
TTCAACGTATTAAGCAACAAGGACTCAACATTAAACCAAGGATTCTCATTCTAACT
CGACTTCTACCTGATGCGGTAGGAACTACATGCGGTGAACGTCTCGAGAGAGTTT
ATGATTCTGAGTACTGTGATATTCTTCGTGTGCCCTTCAGAACAGAGAAGGGTATT
GTTCGCAAATGGATCTCAAGGTTCGAAGTCTGGCCATATCTAGAGACTTACACCGA
GGATGCTGCGGTTGAGCTATCGAAAGAATTGAATGGCAAGCCTGACCTTATCATT
GGTAACTACAGTGATGGAAATCTTGTTGCTTCTTTATTGGCTCACAAACTTGGTGT
CACTCAGTGTACCATTGCTCATGCTCTTGAGAAAACAAAGTACCCGGATTCTGATA
TCTACTGGAAGAAGCTTGACGACAAGTACCATTTCTCATGCCAGTTCACTGCGGAT
ATTTTCGCAATGAACCACACTGATTTCATCATCACTAGTACTTTCCAAGAAATTGC
TGGAAGCAAAGAAACTGTTGGGCAGTATGAAAGCCACACAGCCTTTACTCTTCCC
GGATTGTATCGAGTTGTTCACGGGATTGATGTGTTTGATCCCAAGTTCAACATTGT
CTCTCCTGGTGCTGATATGAGCATCTACTTCCCTTACACAGAGGAGAAGCGTAGAT
TGACTAAGTTCCACTCTGAGATCGAGGAGCTCCTCTACAGCGATGTTGAGAACAA
AGAGCACTTATGTGTGCTCAAGGACAAGAAGAAGCCGATTCTCTTCACAATGGCT
AGGCTTGATCGTGTCAAGAACTTGTCAGGTCTTGTTGAGTGGTACGGGAAGAACA
CCCGCTTGCGTGAGCTAGCTAACTTGGTTGTTGTTGGAGGAGACAGGAGGAAAGA
GTCAAAGGACAATGAAGAGAAAGCAGAGATGAAGAAAATGTATGATCTCATTGA
GGAATACAAGCTAAACGGTCAGTTCAGGTGGATCTCCTCTCAGATGGACCGGGTA
AGGAACGGTGAGCTGTACCGGTACATCTGTGACACCAAGGGTGCTTTTGTCCAAC
CTGCATTATATGAAGCCTTTGGGTTAACTGTTGTGGAGGCTATGACTTGTGGTTTA
CCGACTTTCGCCACTTGCAAAGGTGGTCCAGCTGAGATCATTGTGCACGGTAAATC
GGGTTTCCACATTGACCCTTACCATGGTGATCAGGCTGCTGATACTCTTGCTGATTT
CTTCACCAAGTGTAAGGAGGATCCATCTCACTGGGATGAGATCTCAAAAGGAGGG
```

-continued

```
CTTCAGAGGATTGAGGAGAAATACACTTGGCAAATCTATTCACAGAGGCTCTTGA

CATTGACTGGTGTGTATGGATTCTGGAAGCATGTCTCGAACCTTGACCGTCTTGAG

GCTCGCCGTTACCTTGAAATGTTCTATGCATTGAAGTATCGCCCATTGGCTCAGGC

TGTTCCTCTTGCACAAGATGATTGA
```

WT UGT76G1 from *Stevia rebaudiana*: Amino Acid Sequence:
(SEQ ID NO: 9)

```
MENKTETTVRRRRRIILFPVPFQGHINPILQLANVLYSKGFSITIFHTNFNKPKTSNYPHF

TFRFILDNDPQDERISNLPTHGPLAGMRIPIINEHGADELRRELELLMLASEEDEEVSCLI

TDALWYFAQSVADSLNLRRLVLMTSSLFNFHAHVSLPQFDELGYLDPDDKTRLEEQA

SGFPMLKVKDIKSAYSNWQILKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

VDSKQSFLWVVRPGFVKGSTWVEPLPDGFLGERGRIVKWVPQQEVLAHGAIGAFWT

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSL
```

WT UGT76G1 from *Stevia rebaudiana*: DNA Sequence:
(SEQ ID NO: 10)

```
ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTCTGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

GTTCTTAATTCCACTACCCAAGCACCTTACTGCAAGTAGCAGTTCCCTCCTAGATC

ATGACCGAACCGTGTTTCAGTGGCTGGATCAGCAACCCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTCTGATTTTGGGCTTGACCAGCCTCTAAACGCTCGCTATATGTCT

GATGTGTTGAAGGTTGGCGTGTACCTGGAGAATGGTTGGGAAGGGGGGAAATTG

CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

TATGAATCCCTAGAATCCTTGGTAAGCTATATATCTTCGTTATAA
```

-continued

WT AtSUS1 from *Arabidopsis thaliana*: Amino Acid Sequence:
(SEQ ID NO: 11)

MANAERMITRVHSQRERLNETLVSERNEVLALLSRVEAKGKGILQQNQIIAEFEALPE

QTRKKLEGGPFFDLLKSTQEAIVLPPWVALAVRPRPGVWEYLRVNLHALVVEELQPA

EFLHFKEELVDGVKNGNFTLELDFEPFNASIPRPTLHKYIGNGVDFLNRHLSAKLFHDK

ESLLPLLKFLRLHSHQGKNLMLSEKIQNLNTLQHTLRKAEEYLAELKSETLYEEFEAKF

EEIGLERGWGDNAERVLDMIRLLLDLLEAPDPCTLETFLGRVPMVFNVVILSPHGYFA

QDNVLGYPDTGGQVVYILDQVRALEIEMLQRIKQQGLNIKPRILILTRLLPDAVGTTCG

ERLERVYDSEYCDILRVPFRTEKGIVRKWISRFEVWPYLETYTEDAAVELSKELNGKP

DLIIGNYSDGNLVASLLAHKLGVTQCTIAHALEKTKYPDSDIYWKKLDDKYHFSCQFT

ADIFAMNHTDFIITSTFQEIAGSKETVGQYESHTAFTLPGLYRVVHGIDVFDPKFNIVSP

GADMSIYFPYTEEKRRLTKFHSEIEELLYSDVENKEHLCVLKDKKKPILFTMARLDRV

KNLSGLVEWYGKNTRLRELANLVVVGGDRRKESKDNEEKAEMKKMYDLIEEYKLN

GQFRWISSQMDRVRNGELYRYICDTKGAFVQPALYEAFGLTVVEAMTCGLPTFATCK

GGPAEIIVHGKSGFHIDPYHGDQAADTLADFFTKCKEDPSHWDEISKGGLQRIEEKYT

WQIYSQRLLTLTGVYGFWKHVSNLDRLEARRYLEMFYALKYRPLAQAVPLAQDD

WT AtSUS1 from *Arabidopsis thaliana*: DNA Sequence:
(SEQ ID NO: 12)

ATGGCAAACGCTGAACGTATGATTACCCGTGTCCACTCCCAACGCGAACGCCTGA

ACGAAACCCTGGTGTCGGAACGCAACGAAGTTCTGGCACTGCTGAGCCGTGTGGA

AGCTAAGGGCAAAGGTATTCTGCAGCAAAACCAGATTATCGCGGAATTTGAAGCC

CTGCCGGAACAAACCCGCAAAAAGCTGGAAGGCGGTCCGTTTTTCGATCTGCTGA

AATCTACGCAGGAAGCGATCGTTCTGCCGCCGTGGGTCGCACTGGCAGTGCGTCC

GCGTCCGGGCGTTTGGGAATATCTGCGTGTCAACCTGCATGCACTGGTGGTTGAAG

AACTGCAGCCGGCTGAATTTCTGCACTTCAAGGAAGAACTGGTTGACGGCGTCAA

AAACGGTAATTTTACCCTGGAACTGGATTTTGAACCGTTCAATGCCAGTATCCCGC

GTCCGACGCTGCATAAATATATTGGCAACGGTGTGGACTTTCTGAATCGCCATCTG

AGCGCAAAGCTGTTCCACGATAAAGAATCTCTGCTGCCGCTGCTGAAATTCCTGCG

TCTGCATAGTCACCAGGGCAAGAACCTGATGCTGTCCGAAAAAATTCAGAACCTG

AATACCCTGCAACACACGCTGCGCAAGGCGGAAGAATACCTGGCCGAACTGAAAA

GTGAAACCCTGTACGAAGAATTCGAAGCAAAGTTCGAAGAAATTGGCCTGGAACG

TGGCTGGGGTGACAATGCTGAACGTGTTCTGGATATGATCCGTCTGCTGCTGGACC

TGCTGGAAGCACCGGACCCGTGCACCCTGGAAACGTTTCTGGGTCGCGTGCCGAT

GGTTTTCAACGTCGTGATTCTGTCCCCGCATGGCTATTTTGCACAGGACAATGTGC

TGGGTTACCCGGATACCGGCGGTCAGGTTGTCTATATTCTGGATCAAGTTCGTGCG

CTGGAAATTGAAATGCTGCAGCGCATCAAGCAGCAAGGCCTGAACATCAAACCGC

GTATTCTGATCCTGACCCGTCTGCTGCCGGATGCAGTTGGTACCACGTGCGGTGAA

CGTCTGGAACGCGTCTATGACAGCGAATACTGTGATATTCTGCGTGTCCCGTTTCG

CACCGAAAAGGGTATTGTGCGTAAATGGATCAGTCGCTTCGAAGTTTGGCCGTATC

TGGAAACCTACACGGAAGATGCGGCCGTGGAACTGTCCAAGGAACTGAATGGCAA

ACCGGACCTGATTATCGGCAACTATAGCGATGGTAATCTGGTCGCATCTCTGCTGG

CTCATAAACTGGGTGTGACCCAGTGCACGATTGCACACGCTCTGGAAAAGACCAA

ATATCCGGATTCAGACATCTACTGGAAAAAGCTGGATGACAAATATCATTTTTCGT

-continued

```
GTCAGTTCACCGCGGACATTTTTGCCATGAACCACACGGATTTTATTATCACCAGT

ACGTTCCAGGAAATCGCGGGCTCCAAAGAAACCGTGGGTCAATACGAATCACATA

CCGCCTTCACGCTGCCGGGCCTGTATCGTGTGGTTCACGGTATCGATGTTTTTGAC

CCGAAATTCAATATTGTCAGTCCGGGCGCGGATATGTCCATCTATTTTCCGTACAC

CGAAGAAAGCGTCGCCTGACGAAATTCCATTCAGAAATTGAAGAACTGCTGTAC

TCGGACGTGGAAAACAAGGAACACCTGTGTGTTCTGAAAGATAAAAAGAAACCG

ATCCTGTTTACCATGGCCCGTCTGGATCGCGTGAAGAATCTGTCAGGCCTGGTTGA

ATGGTATGGTAAAAACACGCGTCTGCGCGAACTGGCAAATCTGGTCGTGGTTGGC

GGTGACCGTCGCAAGGAATCGAAAGATAACGAAGAAAAGGCTGAAATGAAGAAA

ATGTACGATCTGATCGAAGAATACAAGCTGAACGGCCAGTTTCGTTGGATCAGCT

CTCAAATGGACCGTGTGCGCAATGGCGAACTGTATCGCTACATTTGCGATACCAA

GGGTGCGTTTGTTCAGCCGGCACTGTACGAAGCTTTCGGCCTGACCGTCGTGGAAG

CCATGACGTGCGGTCTGCCGACCTTTGCGACGTGTAAAGGCGGTCCGGCCGAAAT

TATCGTGCATGGCAAATCTGGTTTCCATATCGATCCGTATCACGGTGATCAGGCAG

CTGACACCCTGGCGGATTTCTTTACGAAGTGTAAAGAAGACCCGTCACACTGGGA

TGAAATTTCGAAGGGCGGTCTGCAACGTATCGAAGAAAAATATACCTGGCAGATT

TACAGCCAACGCCTGCTGACCCTGACGGGCGTCTACGGTTTTTGGAAACATGTGTC

TAATCTGGATCGCCTGGAAGCCCGTCGCTATCTGGAAATGTTTTACGCACTGAAGT

ATCGCCCGCTGGCACAAGCCGTTCCGCTGGCACAGGACGACTAA
```

What is claimed is:

1. A method for synthesizing rebaudioside I, the method comprising preparing a reaction mixture comprising:
   (a) a steviol glycoside composition comprising rebaudioside A;
   (b) a substrate selected from the group consisting of sucrose, uridine diphosphate (UDP), uridine diphosphate-glucose (UDP-glucose), and combinations thereof; and
   (c) a UDP-glycosyltransferase enzyme comprising the amino acid sequence of SEQ ID NO: 1; and
   incubating the reaction mixture for a sufficient time to produce rebaudioside I.

2. The method of claim 1, wherein the steviol glycoside composition is *Stevia* extract.

3. The method of claim 1, further comprising adding a sucrose synthase to the reaction mixture before incubating the reaction mixture for a sufficient time to produce rebaudioside I.

4. The method of claim 3, wherein the sucrose synthase is an *Arabidopsis thaliana* sucrose synthase 1 (AtSUS1) comprising the amino acid sequence of SEQ ID NO: 11.

5. The method of claim 1, wherein the reaction mixture is in vitro.

6. The method of claim 1, wherein the reaction mixture is a cell-based reaction mixture.

7. The method of claim 6, wherein the UDP-glycosyltransferase enzyme is expressed in a host cell.

8. The method of claim 7, wherein the host cell is selected from the group consisting of a yeast, a non-steviol glycoside-producing plant, an alga, a fungus, and a bacterium.

9. The method of claim 7, wherein the host cell is a bacterial cell.

10. The method of claim 9, wherein the bacterial cell is an *E. coli* cell.

11. The method of claim 7, wherein the host cell is a yeast cell.

12. The method of claim 1, wherein the substrate is UDP-glucose.

13. The method of claim 1, wherein the rebaudioside A has a concentration of 15 to 50 g/L in the reaction mixture.

14. The method to claim 1, wherein the reaction mixture has a pH range of 6.5 to 9.5 at a temperature of 35° C. to 45° C.

15. The method of claim 1, further comprising isolating crude rebaudioside I.

16. The method of claim 15, further comprising crystallizing the crude rebaudioside I to obtain rebaudioside I with a purity of greater than 98%.

17. The method of claim 1, wherein the reaction mixture further comprises a sucrose synthase.

* * * * *